US006468743B1

(12) United States Patent
Romick et al.

(10) Patent No.: US 6,468,743 B1
(45) Date of Patent: Oct. 22, 2002

(54) PCR TECHNIQUES FOR DETECTING MICROBIAL CONTAMINANTS IN FOODSTUFFS

(75) Inventors: Thomas L. Romick, Chino Hills; Mark S. Fraser, Fullerton, both of CA (US)

(73) Assignee: ConAgra Grocery Products Company, Fullerton, CA (US)

( * ) Notice: Subject to any disclaimer, the term of this patent is extended or adjusted under 35 U.S.C. 154(b) by 0 days.

(21) Appl. No.: 09/313,221

(22) Filed: May 17, 1999

Related U.S. Application Data

(60) Provisional application No. 60/086,025, filed on May 18, 1998.

(51) Int. Cl.[7] .......................... C12Q 1/68; C12P 19/34; C07H 21/04; G01N 33/53

(52) U.S. Cl. ............................... 435/6; 435/5; 435/7.2; 435/91.1; 435/91.2; 536/23.1; 536/24.3; 536/24.32; 536/26.6

(58) Field of Search .......................... 435/6, 91.2, 91.1, 435/5, 7.2; 536/24.32, 24.3, 26.6, 23.1

(56) References Cited

U.S. PATENT DOCUMENTS

| | | | | |
|---|---|---|---|---|
| 4,683,195 A | | 7/1987 | Mullis et al. | 435/6 |
| 4,683,202 A | | 7/1987 | Mullis et al. | 435/91 |
| 4,800,159 A | | 1/1989 | Mullis et al. | 435/172.3 |
| 4,889,818 A | | 12/1989 | Gelfand et al. | 435/194 |
| 4,965,188 A | | 10/1990 | Mullis et al. | 435/6 |
| 5,210,015 A | | 5/1993 | Gelfand et al. | 435/6 |
| 5,340,728 A | * | 8/1994 | Grosz et al. | 135/91.2 |
| 5,574,142 A | * | 11/1996 | Meyer, Jr. et al. | 536/23.1 |
| 5,846,783 A | * | 12/1998 | Wu et al. | 435/91.2 |
| 5,866,336 A | * | 2/1999 | Nazarenko et al. | 435/6 |
| 5,925,517 A | * | 7/1999 | Tyagi et al. | 435/6 |
| 5,994,066 A | * | 11/1999 | Bergeron et al. | 435/6 |

FOREIGN PATENT DOCUMENTS

| | | | |
|---|---|---|---|
| FR | WO96/24686 | * | 4/1996 |
| WO | WO 89/03891 | | 5/1989 |
| WO | WO 95/13399 | | 5/1995 |

OTHER PUBLICATIONS

Erlich et al. Recent Advances in the Polymerase Chain Reaction Science, 1991, 252: 1643–1650.*

Branlant et al. "Structural study of ribosomal 23 sRNA from *E. coli*" FEBS Letters, 1979, 107(1): 177–181.*

The Polymerase Chain Reaction: Applications for the Detection of Foodborne Pathogens, by Walter E. Hill, 1996.

Applied and Environmental Microbology, Mar. 1997, p. 1019–1023, Use of an Arbitrarily Primed PCR Product in the Development of a *Campylobacter jejuni*–Specific PCR, by Day, et al.

Applied and Evironmenal Microbiology, Mar. 1997, p. 1143–1147, Molecular Beacons: Trial of a Flourescence–Based Solution Hybridization Technique for Ecological Studies with Ruminal Bacteria, by Schofieldet al.

Nature Biotechnology, vol. 14, Mar. 1996, Molecular Beacons: Probes that Fluoresce upon Hybridization, by Tuagi et al.

* cited by examiner

*Primary Examiner*—W. Gary Jones
*Assistant Examiner*—B J Forman
(74) *Attorney, Agent, or Firm*—Christie, Parker & Hale, LLP

(57) ABSTRACT

A method or detecting the presence of living or dead microorganisms and viruses in a sample comprises adding to a pre-determined volume of a sample comprising nucleic acid-containing microbe (s) and/or virus (es), known amounts of a pair of primers binding to sequences up-stream and down-stream to a universal or specific microbial and/or viral nucleic acid sequence and polymerase chain reaction (PCR) reagents, cycling the mixture to amplify the universal or specific microbial and/or viral nucleic acid sequence; adding a polynucleotide comprising a DNA internal segment that is hybridizably complementary to at least a portion of the universal or specific nucleic acid sequence; and a first and a second DNA arm segment adjoining the DNA internal segment, the first DNA arm segment ending in a 5' terminus and the second DNA arm segment ending in a 3' terminus, the arms segments comprising nucleotide sequences such that they are hybridizably complementary to one another. Optionally, the terminus of one arm segment is operatively connected to a fluorogen and the terminus of the other arm segment is operatively connected to a quencher, such that the polynucleotide comprises a "fluorescent beacon."

21 Claims, No Drawings

SEQUENCE LISTING

```
<160> NUMBER OF SEQ ID NOS:  145

<210> SEQ ID NO 1
<211> LENGTH: 38
<212> TYPE: DNA
<213> ORGANISM: Unknown
<220> FEATURE:
<223> OTHER INFORMATION: Universal Sequence for all bacteria
<221> NAME/KEY: unsure
<222> LOCATION: (5)...(33)
<223> OTHER INFORMATION: m at positions 5 and 29; w at position 17; r at
      position 33; m = a or c; w = a or t; r = a or g

<400> SEQUENCE: 1

cagcmgccgc ggtaatwccc gtcaattcmt ttragttt                             38


<210> SEQ ID NO 2
<211> LENGTH: 30
<212> TYPE: DNA
<213> ORGANISM: Unknown
<220> FEATURE:
<223> OTHER INFORMATION: Universal sequence for all bacteria

<400> SEQUENCE: 2

gaagtcgtaa caaggcaagg catccaccgt                                      30


<210> SEQ ID NO 3
<211> LENGTH: 33
<212> TYPE: DNA
<213> ORGANISM: Unknown
<220> FEATURE:
<223> OTHER INFORMATION: Universal sequence for all bacteria
<221> NAME/KEY: unsure
<222> LOCATION: (16)...(16)
<223> OTHER INFORMATION: u at position 16; u; u = uracil

<400> SEQUENCE: 3

gagtttgatc ctggcucact gctgcctccc gta                                  33


<210> SEQ ID NO 4
<211> LENGTH: 40
<212> TYPE: DNA
<213> ORGANISM: Universal Sequence for Eubacteria

<400> SEQUENCE: 4

agagtttgat cctggctcag aaggaggtga tccagccgca                           40


<210> SEQ ID NO 5
<211> LENGTH: 40
<212> TYPE: DNA
<213> ORGANISM: Aeromonas hydrophila
```

-continued

<400> SEQUENCE: 5
ccaaggggtc tgtggcgaca tttcaccggt aacaggattg 40

<210> SEQ ID NO 6
<211> LENGTH: 41
<212> TYPE: DNA
<213> ORGANISM: Brucella spp.

<400> SEQUENCE: 6
tgctaatacc gtatgtgctt taaccgcgac cgggatgtca a 41

<210> SEQ ID NO 7
<211> LENGTH: 35
<212> TYPE: DNA
<213> ORGANISM: Campylobacter jejuni and Campylobacter coli

<400> SEQUENCE: 7
atgggatttc gtattaacga acttgaaccg atttg 35

<210> SEQ ID NO 8
<211> LENGTH: 43
<212> TYPE: DNA
<213> ORGANISM: Campylobacter jejuni, Campylobacter coli, Campylor

<400> SEQUENCE: 8
accttgttac gacttcaccc cagagagttt gatcctggct cag 43

<210> SEQ ID NO 9
<211> LENGTH: 31
<212> TYPE: DNA
<213> ORGANISM: Clostridium spp.

<400> SEQUENCE: 9
gatcctggct caggacgggc ggtgtgtaca a 31

<210> SEQ ID NO 10
<211> LENGTH: 38
<212> TYPE: DNA
<213> ORGANISM: Clostridium spp

<400> SEQUENCE: 10
aaactcaaat gaattgacgg gacgggcggt gtgtacaa 38

<210> SEQ ID NO 11
<211> LENGTH: 42
<212> TYPE: DNA
<213> ORGANISM: Clostridium botulinum
<220> FEATURE:
<221> NAME/KEY: unsure
<222> LOCATION: (19)...(34)
<223> OTHER INFORMATION: w = a or t

<400> SEQUENCE: 11
gatggaacca ccatttgcwa gwacatcwat acawattcct gg 42

<210> SEQ ID NO 12
<211> LENGTH: 45
<212> TYPE: DNA
<213> ORGANISM: Clostridium botulinum

<400> SEQUENCE: 12
gatcctgtaa atggtgttgc aagtcccaat tattataact ttgat 45

-continued

<210> SEQ ID NO 13
<211> LENGTH: 46
<212> TYPE: DNA
<213> ORGANISM: Unknown
<220> FEATURE:
<223> OTHER INFORMATION: Sequence related to coliform bacteria

<400> SEQUENCE: 13
tgaaagctgg ctacaggaag gccggtttat gcagcaacgg acgtca 46

<210> SEQ ID NO 14
<211> LENGTH: 37
<212> TYPE: DNA
<213> ORGANISM: Entamoeba histolytica

<400> SEQUENCE: 14
gcaactactg ttagttacct ccaagatatg ttttaac 37

<210> SEQ ID NO 15
<211> LENGTH: 50
<212> TYPE: DNA
<213> ORGANISM: Escherichia coli

<400> SEQUENCE: 15
gctgggcagc aaactgataa ctctccatca agctgtttgt tcgtccgccg 50

<210> SEQ ID NO 16
<211> LENGTH: 46
<212> TYPE: DNA
<213> ORGANISM: Escherichia coli

<400> SEQUENCE: 16
ttacggcgtt actatcctct ctaggtctcg gtcagatatg tgattc 46

<210> SEQ ID NO 17
<211> LENGTH: 58
<212> TYPE: DNA
<213> ORGANISM: Escherichia coli

<400> SEQUENCE: 17
cctctctata tgcacacgga gctcccagct atattgttga ctgcccggga cttcgacc 58

<210> SEQ ID NO 18
<211> LENGTH: 41
<212> TYPE: DNA
<213> ORGANISM: Escherichia coli

<400> SEQUENCE: 18
tgtgtttgct tgtcttcagc atgcgcgggg tcatggaacg t 41

<210> SEQ ID NO 19
<211> LENGTH: 41
<212> TYPE: DNA
<213> ORGANISM: Escherichia coli

<400> SEQUENCE: 19
ggcgacacat tataccgtgc ccgaattctg ttatatatgt c 41

<210> SEQ ID NO 20
<211> LENGTH: 41
<212> TYPE: DNA
<213> ORGANISM: Escherichia coli

<400> SEQUENCE: 20

-continued tctgtattgt ctttttcacc ttaatagcac ccggtacaag c 41

<210> SEQ ID NO 21
<211> LENGTH: 59
<212> TYPE: DNA
<213> ORGANISM: Escherichia coli
<220> FEATURE:
<221> NAME/KEY: unsure
<222> LOCATION: (20)...(51)
<223> OTHER INFORMATION: n at positions 20, 21, 23, 24, 28, 29, 30, 49, and 50; n = inosine

<400> SEQUENCE: 21 tttttctgt attttctttn ncnncttnnn tcaggcagga ttacaacana nttcacagc 59

<210> SEQ ID NO 22
<211> LENGTH: 50
<212> TYPE: DNA
<213> ORGANISM: Escherichia coli

<400> SEQUENCE: 22
tcgccacacg ctgacgctga ccattacatg acctcgcttt agttcacaga 50

<210> SEQ ID NO 23
<211> LENGTH: 50
<212> TYPE: DNA
<213> ORGANISM: Escherichia coli

<400> SEQUENCE: 23
gacggctgta ctgcagggtg tggcgatatc ctttctgcag ggatgcaata 50

<210> SEQ ID NO 24
<211> LENGTH: 50
<212> TYPE: DNA
<213> ORGANISM: Escherichia coli

<400> SEQUENCE: 24
ctccggagaa ctgggtgcat cttaccggag gagtaattac aaacctggca 50

<210> SEQ ID NO 25
<211> LENGTH: 41
<212> TYPE: DNA
<213> ORGANISM: Escherichia coli

<400> SEQUENCE: 25
accctgtaaa cgaagtttgc gatctcatgc gactacttga c 41

<210> SEQ ID NO 26
<211> LENGTH: 50
<212> TYPE: DNA
<213> ORGANISM: Escherichia coli

<400> SEQUENCE: 26
ttaatagcac ccggtacaag caggcctgac tcttcaaaag agaaaattac 50

<210> SEQ ID NO 27
<211> LENGTH: 40
<212> TYPE: DNA
<213> ORGANISM: Escherichia coli

<400> SEQUENCE: 27
ccggtattac agaaatctga gtgcatgatg aatccagggt 40

<210> SEQ ID NO 28

-continued

<211> LENGTH: 41
<212> TYPE: DNA
<213> ORGANISM: Escherichia coli

<400> SEQUENCE: 28
cagtctatta cagaactatg ccatactgat tgccgcaatt g 41

<210> SEQ ID NO 29
<211> LENGTH: 40
<212> TYPE: DNA
<213> ORGANISM: Escherichia coli

<400> SEQUENCE: 29
gacaggattt gttaacaggt tccagttaca caatcaggcc 40

<210> SEQ ID NO 30
<211> LENGTH: 40
<212> TYPE: DNA
<213> ORGANISM: Escherichia coli

<400> SEQUENCE: 30
acactggatg atctcagtgg ctgaatcccc ctccattatg 40

<210> SEQ ID NO 31
<211> LENGTH: 41
<212> TYPE: DNA
<213> ORGANISM: Escherichia coli

<400> SEQUENCE: 31
ccatgacaac ggacagcagt tcctgtcaac tgagcacttt g 41

<210> SEQ ID NO 32
<211> LENGTH: 50
<212> TYPE: DNA
<213> ORGANISM: Escherichia coli

<400> SEQUENCE: 32
aaatcgccat tcgttgacta cttcttgcca ttctggcaac tcgcgatgca 50

<210> SEQ ID NO 33
<211> LENGTH: 49
<212> TYPE: DNA
<213> ORGANISM: Escherichia coli

<400> SEQUENCE: 33
cagtcgtcac tcactggttt catcaggata ttctccccac tctgacacc 49

<210> SEQ ID NO 34
<211> LENGTH: 41
<212> TYPE: DNA
<213> ORGANISM: Escherichia coli

<400> SEQUENCE: 34
tttacgatag acttttcgac cacatataaa ttatttcgct c 41

<210> SEQ ID NO 35
<211> LENGTH: 40
<212> TYPE: DNA
<213> ORGANISM: Escherichia coli

<400> SEQUENCE: 35
aagaagatgt ttatggcggt cacgaatcag gttatgcctc 40

-continued

<210> SEQ ID NO 36
<211> LENGTH: 40
<212> TYPE: DNA
<213> ORGANISM: Escherichia coli

<400> SEQUENCE: 36
cattcacagt aaaagtggcc gggtgcctcc cggtgagttc 40

<210> SEQ ID NO 37
<211> LENGTH: 48
<212> TYPE: DNA
<213> ORGANISM: Escherichia coli, Salmonella spp., and Shigella sp

<400> SEQUENCE: 37
ctgatcgaat ggctgccagg ctcccaacca gacgatagtt atcacgca 48

<210> SEQ ID NO 38
<211> LENGTH: 37
<212> TYPE: DNA
<213> ORGANISM: Escherichia coli and Shigella spp.

<400> SEQUENCE: 38
taatactcct gaacggcgtt aggtgtcggc ttttctg 37

<210> SEQ ID NO 39
<211> LENGTH: 40
<212> TYPE: DNA
<213> ORGANISM: Escherichia coli and Shigella spp.

<400> SEQUENCE: 39
gaagagtccg tgggattacg agcgatgcag ctattaataa 40

<210> SEQ ID NO 40
<211> LENGTH: 40
<212> TYPE: DNA
<213> ORGANISM: Escherichia coli and Shigella spp.

<400> SEQUENCE: 40
tatggaattt cgccgatttt tgtttgcctc cctgctgcgg 40

<210> SEQ ID NO 41
<211> LENGTH: 43
<212> TYPE: DNA
<213> ORGANISM: Escherichia coli and Shigella spp.

<400> SEQUENCE: 41
tgttacgtcc tgtagaaagc ccaaactgcc tggcacagca att 43

<210> SEQ ID NO 42
<211> LENGTH: 38
<212> TYPE: DNA
<213> ORGANISM: Shigella spp.

<400> SEQUENCE: 42
ctggatggta tggtgagggg aggccaacaa ttatttcc 38

<210> SEQ ID NO 43
<211> LENGTH: 41
<212> TYPE: DNA
<213> ORGANISM: Shigella dysenteriae

<400> SEQUENCE: 43
gttccttgac cgcctttccg atacgccggt cagccaccct c 41

-continued

<210> SEQ ID NO 44
<211> LENGTH: 41
<212> TYPE: DNA
<213> ORGANISM: Giardia spp.

<400> SEQUENCE: 44
aagtgcgtca acgagcagct ttagtgcttt gtgaccatcg a 41

<210> SEQ ID NO 45
<211> LENGTH: 60
<212> TYPE: DNA
<213> ORGANISM: Giardia duodenalis

<400> SEQUENCE: 45
cataacgacg ccatcgcggc tctcaggaat ttgtgagcgc ttctgtcgtg gcagcgctaa 60

<210> SEQ ID NO 46
<211> LENGTH: 40
<212> TYPE: DNA
<213> ORGANISM: Helicobacter pylori

<400> SEQUENCE: 46
ctggagagac taacgggtgg attactgacg ctgattctgc 40

<210> SEQ ID NO 47
<211> LENGTH: 44
<212> TYPE: DNA
<213> ORGANISM: Helicobacter pylori

<400> SEQUENCE: 47
tggcaatcag cgtcaggtaa tggctaagag atcagcctat gtcc 44

<210> SEQ ID NO 48
<211> LENGTH: 36
<212> TYPE: DNA
<213> ORGANISM: Helicobacter pylori

<400> SEQUENCE: 48
gccaatggta aattagttct ccttaattgt ttttac 36

<210> SEQ ID NO 49
<211> LENGTH: 30
<212> TYPE: DNA
<213> ORGANISM: Helicobacter pylori

<400> SEQUENCE: 49
aggaggatga gatgaacttt attggctggt 30

<210> SEQ ID NO 50
<211> LENGTH: 36
<212> TYPE: DNA
<213> ORGANISM: Listeria spp.
<220> FEATURE:
<221> NAME/KEY: unsure
<222> LOCATION: (5)...(17)
<223> OTHER INFORMATION: m at position 5; w at position 17; m = a or c;
w = a or t

<400> SEQUENCE: 50
cagcmgccgc ggtaatwcct ccataaaggt gaccct 36

<210> SEQ ID NO 51
<211> LENGTH: 40
<212> TYPE: DNA

-continued

<213> ORGANISM: Listeria spp.

<400> SEQUENCE: 51
atgaatatga aaaaagcaac ttatacgcga ccgaagccaa 40

<210> SEQ ID NO 52
<211> LENGTH: 40
<212> TYPE: DNA
<213> ORGANISM: Listeria monocytogenes and Listeria innocua

<400> SEQUENCE: 52
gctacagctg ggattgcggt ttatacgcga ccgaagccaa 40

<210> SEQ ID NO 53
<211> LENGTH: 40
<212> TYPE: DNA
<213> ORGANISM: Listeria innocua

<400> SEQUENCE: 53
actagcactc cagttgttaa ttatacgcga ccgaagccaa 40

<210> SEQ ID NO 54
<211> LENGTH: 37
<212> TYPE: DNA
<213> ORGANISM: Listeria invanovii, Listeria seeligeri, and Lister
<220> FEATURE:
<221> NAME/KEY: unsure
<222> LOCATION: (14)...(14)
<223> OTHER INFORMATION: r at position 14; r = a or g

<400> SEQUENCE: 54
ttactgaggt agcragctta tacgcgaccg aagccaa 37

<210> SEQ ID NO 55
<211> LENGTH: 40
<212> TYPE: DNA
<213> ORGANISM: Listeria monocytogenes

<400> SEQUENCE: 55
cacgtgctac aatggataga gaatagtttt atgggattag 40

<210> SEQ ID NO 56
<211> LENGTH: 46
<212> TYPE: DNA
<213> ORGANISM: Listeria monocytogenes

<400> SEQUENCE: 56
catcgacggc aacctcggag aatacaatta ccgttctcca ccattc 46

<210> SEQ ID NO 57
<211> LENGTH: 34
<212> TYPE: DNA
<213> ORGANISM: Listeria monocytogenes

<400> SEQUENCE: 57
aacctatcca ggtgctccgc cacacttgag atat 34

<210> SEQ ID NO 58
<211> LENGTH: 40
<212> TYPE: DNA
<213> ORGANISM: Listeria monocytogenes

<400> SEQUENCE: 58
gcatctgcat tcaataaaga tgtcactgca tctccgtggt 40

-continued

<210> SEQ ID NO 59
<211> LENGTH: 40
<212> TYPE: DNA
<213> ORGANISM: Listeria monocytogenes

<400> SEQUENCE: 59
cggaggttcc gcaaaagatg cctccagagt gatcgatgtt 40

<210> SEQ ID NO 60
<211> LENGTH: 36
<212> TYPE: DNA
<213> ORGANISM: Listeria monocytogenes

<400> SEQUENCE: 60
cctaagacgc caatcgaaaa gcgcttgcaa ctgctc 36

<210> SEQ ID NO 61
<211> LENGTH: 36
<212> TYPE: DNA
<213> ORGANISM: Listeria monocytogenes

<400> SEQUENCE: 61
cctaagacgc caatcgaaaa gcgcttgcaa ctgctc 36

<210> SEQ ID NO 62
<211> LENGTH: 40
<212> TYPE: DNA
<213> ORGANISM: Listeria monocytogenes

<400> SEQUENCE: 62
attgcgaaat ttggtacagc acttgagata tatgcaggag 40

<210> SEQ ID NO 63
<211> LENGTH: 40
<212> TYPE: DNA
<213> ORGANISM: Listeria monocytogenes

<400> SEQUENCE: 63
acaagctgca cctgttgcag tgacagcgtg tgtagtagca 40

<210> SEQ ID NO 64
<211> LENGTH: 39
<212> TYPE: DNA
<213> ORGANISM: Listeria monocytogenes

<400> SEQUENCE: 64
caagcaacta cacctgcgcc gaaccttgtt agcattcgt 39

<210> SEQ ID NO 65
<211> LENGTH: 39
<212> TYPE: DNA
<213> ORGANISM: Listeria monocytogenes

<400> SEQUENCE: 65
acaagctgca cctgttgcag gasccttgtt agcattcgt 39

<210> SEQ ID NO 66
<211> LENGTH: 40
<212> TYPE: DNA
<213> ORGANISM: Listeria monocytogenes

<400> SEQUENCE: 66

-continued cgaatctaac ggctggcaca gcccaaatag tgtcaccgct 40

<210> SEQ ID NO 67
<211> LENGTH: 42
<212> TYPE: DNA
<213> ORGANISM: Listeria monocytogenes

<400> SEQUENCE: 67
caaactgcta acacagctac tgcacttgaa ttgctgttat tg 42

<210> SEQ ID NO 68
<211> LENGTH: 40
<212> TYPE: DNA
<213> ORGANISM: Listeria monocytogenes

<400> SEQUENCE: 68
ccgggagctg ctaaagcggt gccaaaccac cgaaaatacc 40

<210> SEQ ID NO 69
<211> LENGTH: 40
<212> TYPE: DNA
<213> ORGANISM: Listeria monocytogenes

<400> SEQUENCE: 69
gaagcacctt ttgacgaagc gctggtgcta caggtgtttc 40

<210> SEQ ID NO 70
<211> LENGTH: 40
<212> TYPE: DNA
<213> ORGANISM: Listeria monocytogenes

<400> SEQUENCE: 70
aacaaggtct aactgtaaac actatagtca gctacaattg 40

<210> SEQ ID NO 71
<211> LENGTH: 40
<212> TYPE: DNA
<213> ORGANISM: Salmonella spp.

<400> SEQUENCE: 71
ttattaggat cgcgccaggc aaagaataac cgttgttcac 40

<210> SEQ ID NO 72
<211> LENGTH: 39
<212> TYPE: DNA
<213> ORGANISM: Staphylococcus aureus

<400> SEQUENCE: 72
ttggaaacgg ttaaacgaag aaccttccca tcaaaaaca 39

<210> SEQ ID NO 73
<211> LENGTH: 40
<212> TYPE: DNA
<213> ORGANISM: Staphylococcus aureus

<400> SEQUENCE: 73
tcgcatcaaa ctgacaaacg gcaggtactc tataagtgcc 40

<210> SEQ ID NO 74
<211> LENGTH: 50
<212> TYPE: DNA
<213> ORGANISM: Staphylococcus aureus

<400> SEQUENCE: 74

-continued gagagtcaac cagatcctaa accagatacc aaaagctatt ctcattttct 50

<210> SEQ ID NO 75
<211> LENGTH: 50
<212> TYPE: DNA
<213> ORGANISM: Staphylococcus aureus

<400> SEQUENCE: 75
atgaataaga gtcgatttat ttcatttatc cattctttgt tgtaaggtgg 50

<210> SEQ ID NO 76
<211> LENGTH: 50
<212> TYPE: DNA
<213> ORGANISM: Staphylococcus aureus

<400> SEQUENCE: 76
acacccaacg tattagcaga gagcccctgg tgcaggcatc atatcatacc 50

<210> SEQ ID NO 77
<211> LENGTH: 40
<212> TYPE: DNA
<213> ORGANISM: Staphylococcus aureus

<400> SEQUENCE: 77
gacataaaag ctaggaattt aaatcggatt aacattatcc 40

<210> SEQ ID NO 78
<211> LENGTH: 40
<212> TYPE: DNA
<213> ORGANISM: Staphylococcus aureus

<400> SEQUENCE: 78
ctagtttggt aatatctcct taatgctata tcttataggg 40

<210> SEQ ID NO 79
<211> LENGTH: 40
<212> TYPE: DNA
<213> ORGANISM: Staphylococcus aureus

<400> SEQUENCE: 79
tagataaagt taaaacaagc taacttaccg tggacccttc 40

<210> SEQ ID NO 80
<211> LENGTH: 61
<212> TYPE: DNA
<213> ORGANISM: Staphylococcus aureus

<400> SEQUENCE: 80
ttcactattt gtaaaagtgt cagaccccac ttactaatga atttttttat cgtaagccct 60
t 61

<210> SEQ ID NO 81
<211> LENGTH: 40
<212> TYPE: DNA
<213> ORGANISM: Staphylococcus aureus

<400> SEQUENCE: 81
atggcagcat cagcttgata tttccaataa ccacccgttt 40

<210> SEQ ID NO 82
<211> LENGTH: 40
<212> TYPE: DNA

-continued

<213> ORGANISM: Staphylococcus aureus

<400> SEQUENCE: 82
ctagtgcatt tgttattcaa tgcattgaca ccatagtact 40

<210> SEQ ID NO 83
<211> LENGTH: 40
<212> TYPE: DNA
<213> ORGANISM: Staphylococcus aureus

<400> SEQUENCE: 83
acggctatat acattcaatt tccatcgata atatacctaa 40

<210> SEQ ID NO 84
<211> LENGTH: 50
<212> TYPE: DNA
<213> ORGANISM: Staphylococcus aureus

<400> SEQUENCE: 84
agtatatagt gcaacttcaa ctaaaatcag cgttgtcttc gctccaaata 50

<210> SEQ ID NO 85
<211> LENGTH: 45
<212> TYPE: DNA
<213> ORGANISM: Staphylococcus aureus

<400> SEQUENCE: 85
gcgattgatg gtgatacggt tagccaagcc ttgacgaact aaagc 45

<210> SEQ ID NO 86
<211> LENGTH: 48
<212> TYPE: DNA
<213> ORGANISM: Vibrio cholerae

<400> SEQUENCE: 86
ctcagacggg atttgttagg cacgtctatc tctgtagccc ctattacg 48

<210> SEQ ID NO 87
<211> LENGTH: 40
<212> TYPE: DNA
<213> ORGANISM: Vibrio cholerae

<400> SEQUENCE: 87
cgggcagatt ctagaccttc gcaccccaaa tagaactcga 40

<210> SEQ ID NO 88
<211> LENGTH: 45
<212> TYPE: DNA
<213> ORGANISM: Vibrio cholerae

<400> SEQUENCE: 88
cgggcagatt ctagacctcc tgcgatgatc ttggagcatt cccac 45

<210> SEQ ID NO 89
<211> LENGTH: 62
<212> TYPE: DNA
<213> ORGANISM: Vibrio cholerae

<400> SEQUENCE: 89
tgaaataaag cagtcaggtg gtgattctgc acacaaatca gggtattctg cacacaaatc 60
ag 62

-continued

<210> SEQ ID NO 90
<211> LENGTH: 56
<212> TYPE: DNA
<213> ORGANISM: Vibrio cholerae

<400> SEQUENCE: 90
ggaagcttcc aatgattcta agctggatgg gaattctcag gcgtccctac tgggtt 56

<210> SEQ ID NO 91
<211> LENGTH: 42
<212> TYPE: DNA
<213> ORGANISM: Vibrio parahaemolyticus

<400> SEQUENCE: 91
ctgtcccttt tcctgccccc ggctcttagc tgcggcggtg gt 42

<210> SEQ ID NO 92
<211> LENGTH: 48
<212> TYPE: DNA
<213> ORGANISM: Vibrio vulnificus

<400> SEQUENCE: 92
cgccgctcac tggggcactg gctgccagcc gttaagcgaa ccacccgc 48

<210> SEQ ID NO 93
<211> LENGTH: 39
<212> TYPE: DNA
<213> ORGANISM: Vibrio vulnificus

<400> SEQUENCE: 93
ccgcggtaca ggttggcgca cgccacccac tttcgggcc 39

<210> SEQ ID NO 94
<211> LENGTH: 38
<212> TYPE: DNA
<213> ORGANISM: Yersinia enterocolitica

<400> SEQUENCE: 94
gaactcgatg ataactgggg caattcaacc cacttcaa 38

<210> SEQ ID NO 95
<211> LENGTH: 40
<212> TYPE: DNA
<213> ORGANISM: Yersinia enterocolitica

<400> SEQUENCE: 95
actcgatgat aactggggag cccccagtaa tccataaagg 40

<210> SEQ ID NO 96
<211> LENGTH: 42
<212> TYPE: DNA
<213> ORGANISM: Yersinia enterocolitica

<400> SEQUENCE: 96
ttaatgtgta cgctgcgagt gggagtattc atatgaagcg tc 42

<210> SEQ ID NO 97
<211> LENGTH: 40
<212> TYPE: DNA
<213> ORGANISM: Yersinia enterocolitica

<400> SEQUENCE: 97
ctattggtta tgcgcaaagc tggaagtggg ttgaattgca 40

-continued

<210> SEQ ID NO 98
<211> LENGTH: 42
<212> TYPE: DNA
<213> ORGANISM: Yersinia enterocolitica

<400> SEQUENCE: 98
aatgctgtct tcatttggag cgcaacatac atcacagcaa tc 42

<210> SEQ ID NO 99
<211> LENGTH: 38
<212> TYPE: DNA
<213> ORGANISM: Yersinia enterocolitica

<400> SEQUENCE: 99
aaagatattt ttgttcttgt gcagccagca cacgcggg 38

<210> SEQ ID NO 100
<211> LENGTH: 42
<212> TYPE: DNA
<213> ORGANISM: Yersinia pseudotuberculosis

<400> SEQUENCE: 100
taagggtact atcgaggcgg acgtgaaatt aaccgtcaca ct 42

<210> SEQ ID NO 101
<211> LENGTH: 42
<212> TYPE: DNA
<213> ORGANISM: Unknown
<220> FEATURE:
<223> OTHER INFORMATION: Yersinia virulence plasma

<400> SEQUENCE: 101
tcatggcaga acagcagtca gactcatctt accattaaga ag 42

<210> SEQ ID NO 102
<211> LENGTH: 41
<212> TYPE: DNA
<213> ORGANISM: Unknown
<220> FEATURE:
<223> OTHER INFORMATION: Yersinia virulence plasma

<400> SEQUENCE: 102
catggcagaa cagcagtcag actcatctta ccattaagaa g 41

<210> SEQ ID NO 103
<211> LENGTH: 36
<212> TYPE: DNA
<213> ORGANISM: Norwalk virus

<400> SEQUENCE: 103
attgagagcc tccgcgtggg tggcgaagcg gccctc 36

<210> SEQ ID NO 104
<211> LENGTH: 40
<212> TYPE: DNA
<213> ORGANISM: Norwalk virus

<400> SEQUENCE: 104
cttgttggtt tgaggccata tataaaagtt ggcatgaaca 40

<210> SEQ ID NO 105
<211> LENGTH: 42
<212> TYPE: DNA
<213> ORGANISM: Norwalk virus -continued

<400> SEQUENCE: 105
caaattatga cagaatcctt cgagaaatat gacatggatt gc 42

<210> SEQ ID NO 106
<211> LENGTH: 39
<212> TYPE: DNA
<213> ORGANISM: Norwalk virus

<400> SEQUENCE: 106
caccaccata aacaggctga gcctgataga gcattcttt 39

<210> SEQ ID NO 107
<211> LENGTH: 56
<212> TYPE: DNA
<213> ORGANISM: Rotavirus (group A)

<400> SEQUENCE: 107
ggctttaaaa gagagaattt ccgtctgggg tcacatcata caattcctaa tctaag 56

<210> SEQ ID NO 108
<211> LENGTH: 38
<212> TYPE: DNA
<213> ORGANISM: Rotavirus

<400> SEQUENCE: 108
ccatatcagc caacgagttt actacttcta catcaggt 38

<210> SEQ ID NO 109
<211> LENGTH: 40
<212> TYPE: DNA
<213> ORGANISM: Rotavirus

<400> SEQUENCE: 109
cataccaacc aaccactttc tgatgtcata tttactgtgt 40

<210> SEQ ID NO 110
<211> LENGTH: 44
<212> TYPE: DNA
<213> ORGANISM: Rotavirus (group A)

<400> SEQUENCE: 110
ggcttttaaa cgaagtcttc tcaacaatgc gtctaagttc acag 44

<210> SEQ ID NO 111
<211> LENGTH: 38
<212> TYPE: DNA
<213> ORGANISM: Hepatitis A virus

<400> SEQUENCE: 111
tcccagagct ccattgaaca ttatttcatg ctcctcag 38

<210> SEQ ID NO 112
<211> LENGTH: 34
<212> TYPE: DNA
<213> ORGANISM: Hepatitis A virus

<400> SEQUENCE: 112
acaggtatac aaagtcagct ccagaatgat ctcc 34

<210> SEQ ID NO 113
<211> LENGTH: 34
<212> TYPE: DNA

-continued

```
<213> ORGANISM: Hepatitus A virus

<400> SEQUENCE: 113

ctccagaatc atctccacag gtatacaaag tcag                              34


<210> SEQ ID NO 114
<211> LENGTH: 44
<212> TYPE: DNA
<213> ORGANISM: Unknown
<220> FEATURE:
<223> OTHER INFORMATION: Related to Entoviruses

<400> SEQUENCE: 114

cctccggccc ctgaatgcgg ctaattaaca gtggattcgt cggt                   44


<210> SEQ ID NO 115
<211> LENGTH: 7
<212> TYPE: DNA
<213> ORGANISM: Unknown
<220> FEATURE:
<223> OTHER INFORMATION: Universal bacteria-specific nucleic acid
      sequence

<400> SEQUENCE: 115

atcttcg                                                             7


<210> SEQ ID NO 116
<211> LENGTH: 7
<212> TYPE: DNA
<213> ORGANISM: Unknown
<220> FEATURE:
<223> OTHER INFORMATION: Universal bacteria-specific nucleic acid
      sequence

<400> SEQUENCE: 116

cgaagat                                                             7


<210> SEQ ID NO 117
<211> LENGTH: 21
<212> TYPE: DNA
<213> ORGANISM: Artificial Sequence
<220> FEATURE:
<223> OTHER INFORMATION: Beacon sequence

<400> SEQUENCE: 117

ccaccgacga agattcggtg g                                            21


<210> SEQ ID NO 118
<211> LENGTH: 5
<212> TYPE: DNA
<213> ORGANISM: Artificial Sequence
<220> FEATURE:
<223> OTHER INFORMATION: Beacon sequence

<400> SEQUENCE: 118

gctag                                                               5


<210> SEQ ID NO 119
<211> LENGTH: 5
<212> TYPE: DNA
<213> ORGANISM: Artificial Sequence
<220> FEATURE:
<223> OTHER INFORMATION: Beacon sequence

<400> SEQUENCE: 119

ctagc                                                               5
```

-continued

<210> SEQ ID NO 120
<211> LENGTH: 16
<212> TYPE: DNA
<213> ORGANISM: Unknown
<220> FEATURE:
<223> OTHER INFORMATION: Primer sequences complementary to a conserved region of a bacterial small ribosomal RNA operon

<400> SEQUENCE: 120
gctaaggtcc caaagt 16

<210> SEQ ID NO 121
<211> LENGTH: 16
<212> TYPE: DNA
<213> ORGANISM: Unknown
<220> FEATURE:
<223> OTHER INFORMATION: Primer sequences complementary to a conserved region of a bacterial small ribosomal RNA operon

<400> SEQUENCE: 121
agaacgctct cctacc 16

<210> SEQ ID NO 122
<211> LENGTH: 11
<212> TYPE: DNA
<213> ORGANISM: Unknown
<220> FEATURE:
<223> OTHER INFORMATION: Polynucleotide sequence from conserved region of bacterial small ribosomal RNA operon encoding a 23S rRNA

<400> SEQUENCE: 122
cttagaagca g 11

<210> SEQ ID NO 123
<211> LENGTH: 25
<212> TYPE: DNA
<213> ORGANISM: Universal microbial nucleotide sequence

<400> SEQUENCE: 123
cctgcacggg cggtgtgtac gcagg 25

<210> SEQ ID NO 124
<211> LENGTH: 28
<212> TYPE: DNA
<213> ORGANISM: Ruminococcus albus 8

<400> SEQUENCE: 124
cccccgtcat gcggcttcgt tatggggg 28

<210> SEQ ID NO 125
<211> LENGTH: 32
<212> TYPE: DNA
<213> ORGANISM: Fibrobacter succinogenes S85

<400> SEQUENCE: 125
gctgcctgcc cctgaactat ccaagaggca gc 32

<210> SEQ ID NO 126
<211> LENGTH: 10
<212> TYPE: DNA
<213> ORGANISM: Compylobacter jejuni

<400> SEQUENCE: 126
agtcagccac 10

-continued

<210> SEQ ID NO 127
<211> LENGTH: 20
<212> TYPE: DNA
<213> ORGANISM: Compylobacter jejuni

<400> SEQUENCE: 127
atcgggctgt tatgatgata 20

<210> SEQ ID NO 128
<211> LENGTH: 10
<212> TYPE: DNA
<213> ORGANISM: Compylobacter jejuni

<400> SEQUENCE: 128
aatcgggatg 10

<210> SEQ ID NO 129
<211> LENGTH: 20
<212> TYPE: DNA
<213> ORGANISM: Compylobacter jejuni

<400> SEQUENCE: 129
atcactgggg gagctaatat 20

<210> SEQ ID NO 130
<211> LENGTH: 10
<212> TYPE: DNA
<213> ORGANISM: Compylobacter jejuni

<400> SEQUENCE: 130
aggggtcttg 10

<210> SEQ ID NO 131
<211> LENGTH: 23
<212> TYPE: DNA
<213> ORGANISM: Compylobacter jejuni

<400> SEQUENCE: 131
taaggttaaa gttgttgtga atc 23

<210> SEQ ID NO 132
<211> LENGTH: 10
<212> TYPE: DNA
<213> ORGANISM: Compylobacter jejuni

<400> SEQUENCE: 132
agccagcgaa 10

<210> SEQ ID NO 133
<211> LENGTH: 20
<212> TYPE: DNA
<213> ORGANISM: Compylobacter jejuni

<400> SEQUENCE: 133
catatccaga gcctctggat 20

<210> SEQ ID NO 134
<211> LENGTH: 10
<212> TYPE: DNA
<213> ORGANISM: Compylobacter jejuni

<400> SEQUENCE: 134

-continued

```
gaaacgggtg                                                            10


<210> SEQ ID NO 135
<211> LENGTH: 23
<212> TYPE: DNA
<213> ORGANISM: Compylobacter jejuni

<400> SEQUENCE: 135

gtagcctctt catcgtcgtc taa                                             23


<210> SEQ ID NO 136
<211> LENGTH: 10
<212> TYPE: DNA
<213> ORGANISM: Compylobacter jejuni

<400> SEQUENCE: 136

gtgacgtagg                                                            10


<210> SEQ ID NO 137
<211> LENGTH: 20
<212> TYPE: DNA
<213> ORGANISM: Compylobacter jejuni

<400> SEQUENCE: 137

cacccgcttt aacgccaaga                                                 20


<210> SEQ ID NO 138
<211> LENGTH: 7
<212> TYPE: DNA
<213> ORGANISM: Unknown
<220> FEATURE:
<223> OTHER INFORMATION: Universal microbial nucleotide sequence

<400> SEQUENCE: 138

tagaagc                                                                7


<210> SEQ ID NO 139
<211> LENGTH: 16
<212> TYPE: DNA
<213> ORGANISM: Artificial Sequence
<220> FEATURE:
<223> OTHER INFORMATION: Oligonucleotide primer sequence

<400> SEQUENCE: 139

actttgggac cttagc                                                     16


<210> SEQ ID NO 140
<211> LENGTH: 6
<212> TYPE: DNA
<213> ORGANISM: Unknown
<220> FEATURE:
<223> OTHER INFORMATION: Universal bacteria-specific nucleotide sequence

<400> SEQUENCE: 140

tagaac                                                                 6


<210> SEQ ID NO 141
<211> LENGTH: 21
<212> TYPE: DNA
<213> ORGANISM: Artificial Sequence
<220> FEATURE:
<223> OTHER INFORMATION: Oligonucleotide probe sequence

<400> SEQUENCE: 141

ggtggctgct tctaagccac c                                               21
```

-continued

```
<210> SEQ ID NO 142
<211> LENGTH: 16
<212> TYPE: DNA
<213> ORGANISM: Artificial Sequence
<220> FEATURE:
<223> OTHER INFORMATION: Probe

<400> SEQUENCE: 142

ggtaggagag cgttct                                                16


<210> SEQ ID NO 143
<211> LENGTH: 7
<212> TYPE: DNA
<213> ORGANISM: Artificial Sequence
<220> FEATURE:
<223> OTHER INFORMATION: Probe

<400> SEQUENCE: 143

gcttcta                                                           7


<210> SEQ ID NO 144
<211> LENGTH: 21
<212> TYPE: DNA
<213> ORGANISM: Artificial Sequence
<220> FEATURE:
<223> OTHER INFORMATION: Probe

<400> SEQUENCE: 144

ccaccgaatc ttcgtcggtg g                                          21


<210> SEQ ID NO 145
<211> LENGTH: 44
<212> TYPE: DNA
<213> ORGANISM: Escherichia coli and Shigella spp.

<400> SEQUENCE: 145

tgttacgtcc tgtagaaagc ccaaaactgc ctggcacagc aatt                 44
```

PCR TECHNIQUES FOR DETECTING MICROBIAL CONTAMINANTS IN FOODSTUFFS

This invention claims priority based on Ser. No. 60/086,025, filed May 18, 1998.

BACKGROUND OF THE INVENTION

1. Field of the Invention

The present invention relates to a novel technology provided in the form of novel primers, probes, and beacons, and their use in a rapid and accurate assay and kit for assaying for the presence of a microorganism or virus, particularly a bacterium, in a sample. More specifically, this invention relates to an accurate method for assessing microbial, e. g. bacterial or viral, contamination of sterile substances, such as sterile foods, by microorganisms and/or viruses relying on PCR and fluorescent beacon technologies.

2. Description of the Background

Beacons are fluorescent probes which contain short complementary sequences of nucleotide, (arms) attached to the 5' and 3' ends of a probe of a sequence complementary to a target nucleic acid. In addition, the beacon comprises a fluor, fluorophore or fluorogen (fluorogenic agent) and a quencher attached, e. g. via linkers, to the ends of the stem or arms. In the absence of a target, the fluor and the quencher remain close to one another held in place by a hairpin loop stem formed by hybridization of the arms. In this conformation, the beacon does not fluoresce because of quenching. However, when the segment encompassed by the loop hybridizes to a complementary sequence, the hybridization of the arms is prevented, the fluor, fluorophore or fluorogenic agent and the quencher are held apart and fluorescence appears. Thus, the appearance of fluorescence is an indication of hybridization of the probe (DNA internal segment of the beacon) to a complementary nucleic acid sequence of a target. The annealing of a strand of nucleic acid to its complement, thus, may now be measured by following changes in the physical properties of the nucleic acids which occur upon hybridization.

Prior technology utilized, and immobilized the hybridized strands onto, a solid surface, removed unhybridized probes and then determined the number of probes attached to the solid phase. The need for removal of unhybridized probes precluded the application of solid phase hybridization to real time studies involving hybridization of nucleic acids. In addition, solid phase technology also has sensitivity limitations because the probes also bind non-specifically to the solid phase.

In the past the detection of microorganisms was made, generally, by phenotypic observation. Upon the realization that all living cells contain DNA and that DNA is responsible for the expression of phenotypic traits, novel detection methods relying on genetic parameters have been implemented. The polymerase chain reaction (PCR), a relatively recent technological development for amplification of DNA, provides significantly higher sensitivity and, thus, permits the detection of smaller quantities of nucleic acid by amplification and subsequent visualization, for instance, after electrophoretic separation and staining. Fluorescent dyes are also utilized by, for example, attachment to complementary oligomers (hybridization) that bind PCR-amplified DNA. These and other detection technologies eliminate the need for naked eye visualization of PCR products and, therefore, eliminate the need to electrophorese the nucleic acids, except for determining their molecular weight.

As is known in the art, the fidelity of specific DNA sequences produced by PCR is controlled by the primer DNA sequences used and by reaction conditions, such as thermocycling parameters, and the composition of the reaction mixture. DNA primers are generally designed to target specific sites vicinal to a desired sequence and applied to obtain DNA products of complementary sequences by the PCR, along with specifically tailored fluorescent molecular beacons designed to detect only the PCR product.

The detection of pathogens in edible products, cosmetics, medical fluids such as blood and IV solutions, and other products involved in commerce, is of great importance to avoid costly contamination, which may lead to outbreaks of disease and/or the need to discard large batches even after distribution. In most cases, even the etiological agent remains unidentified because of the sparcity of adequate testing technology to do this. Traditional technologies for recovering microorganisms from, for example, a foodstuff might include homogenization of the product in a buffered solution, inoculation of the homogenate in a selective enrichment medium, long hours of incubation at controlled temperatures, streaking of the broth onto a selective and/or differential agar medium, another incubation, isolation of colonies and finally a multiplicity of tests for biochemical or immunological characteristics and microscopic examination. Virulence is mostly tested on pure cultures which require several days of incubation. In addition, for sterility testing, the mere detection of biologically active DNA is critical.

Accordingly, there is a need for a rapid, simple, inexpensive and sensitive method for the general detection of microorganisms and/or viruses in commercial products as well as in pure cultures of microorganisms and viruses.

SUMMARY OF THE INVENTION

This invention relates to an in vitro method of detecting the presence of a microbe or a virus in a food sample, comprising the steps of:

(a) forming a polymerase chain reaction mixture by combining (1) a predetermined volume of a food sample to be tested for the presence of a nucleic acid sequence comprising a universal or specific nucleic acid sequence indicative of a microbe or a virus and sequences upstream and downstream of the universal or specific nucleic acid sequence, (2) known amounts of a first nucleic acid primer and a second nucleic acid primer for binding to the upstream sequence and the downstream sequence, respectively, and (3) polymerase chain reaction reagents;

(b) forming a polymerase chain reaction product by cycling the polymerase chain reaction mixture under conditions effective to amplify the universal or specific nucleic sequence, if present, to replicate and attain about 0.25 to about 10,000 $\mu$g nucleotide product/$\mu$l mixture; and (c) determining whether or not the universal or specific nucleic acid sequence is present in the polymerase chain reaction product, the presence of the universal or specific nucleic acid sequence being indicative of the presence of a microbe or a virus in the food sample.

Any suitable method is used to determine the presence of the universal or specific nucleic acid sequence is present in the polymerase chain reaction product. Fluorescent intercalating reagents, such as ethidium bromide, can be used in conjunction with a fluorescence detection system. Alternatively, suitable oligonucleotide primers(s) that are hybridizably complementary to at least a portion of the reaction product, and bearing a fluorescent label and/or quencher can also be used in conjunction with the PCR amplification and/or fluorescence detection system as known in the art.

This invention also relates to an in vitro method of detecting the presence of a microbe or a virus in a food sample, comprising:

adding to a pre-determined volume of a sample suspected of comprising nucleic acid-containing microbe(s), known amounts of a pair of primers binding to sequences up-stream and down-stream to a universal or specific microbial and/or viral nucleic acid sequence and polymerase chain reaction (PCR) reagents to form a mixture;

cycling the mixture about under conditions effective to amplify the universal or specific microbial and/or viral nucleic acid sequence to attain about 0.25 to about 10,000 $\mu$g universal microbial nucleic acid/$\mu$l mixture;

adding a polynucleotide comprising a DNA internal segment that is hybridizably complementary to at least a portion of the universal or specific nucleic acid sequence; and a first and a second DNA arm segment adjoining the DNA internal segment, the first DNA arm segment ending in a 5' terminus and the second DNA arm segment ending in a 3' terminus, the arms segments comprising nucleotide sequences such that they are hybridizably complementary to one another. Optionally, the terminus of one arm segment is operatively connected to a fluorogen and the terminus of the other arm segment is operatively connected to a quencher, such that the polynucleotide comprises a "fluorescent beacon." The polynucleotide can form a stem-loop structure when there is no universal or specific microbial and/or viral nucleic acid present in the sample. A change in conformation of the stem-loop structure is detected by a fluorescent detection system; and detecting fluorescence emitted by the sample. Any suitable reagent containing a fluorogen or fluorogenic agent, such as fluoroscein, or an intercalating agent, such as ethidium bromide, can be used in detecting a conformational change in the polynucleotide. The reagent can also be a suitable oligonucleotide bearing a fluorescent label.

Alternatively, the polynucleotide is a "fluorescent beacon." When no universal or specific microbial and/or viral nucleic acid is present and replicated by PCR in the sample, the DNA internal segment of the fluorescent beacon is single stranded, the complementary sequences of the arms are hybridized to one another and the fluorogenic agent is quenched by the quencher; when there is microbial and/or viral DNA in the sample, a portion of the universal or specific microbial and/or viral nucleic acid is hybridized to the internal segment of the beacon, and the fluorogenic agent fluoresces.

This invention also relates to a kit for detecting a microbe or virus. The detection kit comprises primers binding to sequences up-stream and down-stream to universal of specific microbial and/or viral nucleic acid sequence (s) and polymerase chain reaction (PCR) reagents; a polynucleotide comprising a DNA internal segment that is hybridizably complementary to at least a portion of the universal or specific nucleic acid sequence; and a first and a second DNA arm segment adjoining the DNA internal segment, the first DNA arm segment ending in a 5' terminus and the second DNA arm segment ending in a 3' terminus, the arms segments comprising nucleotide sequences such that they are hybridizably complementary to one another. Optionally, the terminus of one arm segment is operatively connected to a fluorogen and the terminus of the other arm segment is operatively connected to a quencher, such that the polynucleotide comprises a "fluorescent beacon." The polynucleotide can form a stem-loop structure when there is no universal or specific microbial and/or viral nucleic acid present in the sample. A change in conformation of the stem-loop structure is detected by a fluorescent detection system. The kit also contains instructions for use of the kit to detect the presence of a microbe (s) and/or virus (es), in particular bacteria, and the kit optionally contains PCR reagents.

DETAILED DESCRIPTION OF THE PREFERRED EMBODIMENTS

This invention arose from the desire by the inventors to improve on prior art technology for assessing in a short time whether a sample is contaminated with microorganisms or viruses in an accurate and simple manner. This invention provides an assay and detection kit combining the benefits of nucleic acid amplification by PCR, the specificity of DNA hybridization probes and the signal amplification capability of fluorescent molecular beacon technologies to detect the presence of microorganisms and/or viruses in a product without needing to separate unbound beacon molecules.

This invention relates to an in vitro method of detecting the presence of a microbe or a virus in a food sample, comprising the steps of:

(a) forming a polymerase chain reaction mixture by combining (1) a predetermined volume of a food sample to be tested for the presence of a nucleic acid sequence comprising a universal or specific nucleic acid sequence indicative of a microbe or a virus and sequences upstream and downstream of the universal or specific nucleic acid sequence, (2) known amounts of a first nucleic acid primer and a second nucleic acid primer for binding to the upstream sequence and the downstream sequence, respectively, and (3) polymerase chain reaction reagents;

(b) forming a polymerase chain reaction product by cycling the polymerase chain reaction mixture under conditions effective to amplify the universal or specific nucleic sequence, if present, to replicate and attain about 0.25 to about 10,000 $\mu$g nucleotide product/$\mu$l mixture;. and (c) determining whether or not the universal or specific nucleic acid sequence is present in the polymerase chain reaction product, the presence of the universal or specific nucleic acid sequence being indicative of the presence of a microbe or a virus in the food sample.

Any suitable method is used to determine the presence of the universal or specific nucleic acid sequence is present in the polymerase chain reaction product. Fluorescent intercalating agents, such as ethidium bromide, can be used in conjunction with a fluorescence detection system. Alternatively, a suitable oligonucleotide primer(s) that is hybridizably complementary to at least a portion of the reaction product, and bears a fluorescent label and/or quencher can also be used in conjunction with the PCR amplification or the fluorescence detection system. For example, when the universal or specific nucleic acid sequence is 5'-TAGAAGC-3' (SEQ. ID NO: 138), suitable oligonucleotide primers(s) for purposes of amplification and/or detection of amplification reaction products include 5'-GCTAAGGTCCCAAAGT-3' (SEQ. ID NO. 120), which is usefully labeled with a fluorogen, such as fluoroscein, at its 5'-end, and/or 5'-ACTTTGGGACCTTAGC-3' (SEQ. ID NO. 134), which can also be usefully labeled at its 3'-end with a quencher, such as dabcyl, to quench unhybridized fluorogen-labeled primer in the reaction mix.

The present method also provides a broadly applicable in vitro method of detecting the presence of one or more microbe (s) and/or virus (es) in a sample, which comprises adding to a pre-determined volume of a sample suspected of comprising nucleic acid-containing microbe(s) known amounts of a pair of primers binding to sequences up-stream and down-stream to a universal microbial and viral nucleic acid sequence and polymerase chain reaction (PCR) reagents to form a mixture;

cycling the mixture under conditions effective to amplify the universal microbial and/or viral nucleic acid sequence to attain about 0.25 to about 10,000 $\mu$g universal microbial nucleic acid/$\mu$l mixture;

adding a polynucleotide comprising a DNA internal segment that is hybridizably complementary to at least a portion of the universal or specific nucleic acid sequence; and a first and a second DNA arm segment adjoining the DNA internal segment, the first DNA arm segment ending in a 5' terminus and the second DNA arm segment ending in a 3' terminus, the arms segments comprising nucleotide sequences such that they are hybridizably complementary to one another. Optionally, the terminus of one arm segment is operatively connected to a fluorogen and the terminus of the other arm segment is operatively connected to a quencher, such that the polynucleotide comprises a "fluorescent beacon." The polynucleotide can form a stem-loop structure when there is no universal or specific microbial and/or viral nucleic acid present in the sample. A change in conformation of the stem-loop structure is detected by a fluorescent detection system and detecting any fluorescence emitted by the sample, wherein when no universal microbial and/or viral nucleic acid is present and replicated by PCR in the sample the internal DNA segment remains single stranded. Any suitable reagent containing a fluorogen or fluorogenic agent, such as fluoroscein, or ethidium bromide can be used in detecting a conformational change in the polynucleotide. The reagent can also be a suitable oligonucleotide primer, bearing a fluorescent label or quencher, as described above.

If the polynucleotide is a "fluorescent beacon," the complementary sequences of the extension arms are hybridized to one another and the fluorophore or fluorogenic agent is quenched by the quencher, and when there is microbial and/or viral DNA in the sample, its universal microbial and/or viral nucleic acid sequence is hybridized to the internal segment of the beacon and the fluorogenic agent fluoresces.

As already described above, the polynucleotide (or beacon) is a single stranded nucleic acid molecule possessing a stem and loop structure, where the loop is a probe with a sequence which is complementary to a pre-determined sequence in a target nucleic acid. The stem, on the other hand, is formed by the annealing of two complementary arm segment sequences placed on both sides of the probe segment (DNA internal segment of the polynucleotide) and which DNA arm segment sequences are unrelated to the target sequence to avoid hybridization. Typically, the 5' and 3' ends of the arms are attached, respectively, to a fluorescent moiety and to a non-fluorescent quenching moiety to form a "fluorescent beacon" structure. Thus, the stem portion of the stem and loop structure keeps these two moieties in close proximity and, thereby, quenches any fluorescence by the fluor, fluorophore or fluorogenic agent. When the probe segment encounters a target molecule and hybridizes to it to form a more stable, double stranded structure than the stem and loop structure. The existence of the two structures is precluded by the relative rigidity of nucleic acid structures. Thus, when the probe encounters a complementary sequence, it undergoes a spontaneous conformational change that opens up the stem and forces the arms apart from one another, and, thereby, causes the separation of the fluorophore or fluorogen (or fluorogenic agent) and the quencher and permits, upon incidence of ultraviolet light, the fluorophore to fluoresce. Moreover, because unhybridized beacons are quenched, it is not necessary to remove them from the medium to detect by fluorescence the presence of specific nucleic acids in homogeneous phase and in living cells.

In one preferred embodiment, the DNA internal segment and the two DNA arm segments are complementary to a contiguous universal microbial nucleic acid sequence, and more preferably the DNA internal segment is about 7 to 19 nucleotides long, more preferably about 9 to 15, and still more preferably about 11 to 13 nucleotides long, each DNA arm segment is preferably about 5 to 9 nucleotides long, more preferably about 6 to 8 nucleotides long, and still more preferably 7 nucleotides long, and each primer is preferably about 10 to 20 nucleotides long, more preferably about 12 to 18, and still more preferably about 14 to 16 nucleotides long. In one of the most preferred embodiments the polynucleotide comprises one arm segment with at least one C or G nucleotide(s) at the 5' terminus and the other arm segment with a similar number of complementary nucleotide(s) of the 3' terminus. In this manner, the arm segments strongly hybridize by formation of at least one G:C pair to, thereby, prevent sliding of the DNA segment. The DNA arm segments comprise any possible combination of C, A, T and G nucleotides, and preferably about I to 8 C or G at the 5' terminus and a similar number of complementary nucleotides at the 3' terminus, more preferably about 1 to 3 C or G nucleotide at the 5' terminus and I to 3 complementary nucleotides at the 3' terminus, still more preferably 2 to 6 C or G nucleotides at the 5' terminus and 2 to 6 complementary nucleotide at the 3' terminus. In addition, the polynucleotide's arm segments may further comprise at least one A or T nucleotide(s) vicinal to the C or G nucleotide(s) located at the 5' terminus in a similar number of complementary nucleotide(s) vicinal to the G or C nucleotide(s) at the 3' terminus. In this manner, the hybridization of the arm segments is further reinforced by formation of one or more A:T pairs next to the one or more terminal G:C pairs, preferably the polynucleotide's arm segments comprise 1 to 4 A or T nucleotide vicinal to the C or G nucleotide at the 5' terminus and I to 4 complementary nucleotide(s) thereto which are vicinal to the G or C nucleotide at the 3' terminus, and still more preferably about 2 to 3 A or T nucleotides and 2 to 3 complementary nucleotides.

In another preferred embodiment of the invention, the DNA arm segments are complementary to one another, but at least one of them is not hybridizably complementary the universal microbial or viral nucleic acid sequence. Such non-complementary arm segments are known as "false arms." In this embodiment, the DNA internal segment is preferably about 7 to 19 nucleotides long, more preferably 10 to 15 nucleotides long, and still more preferably 12 to 14 nucleotides long, each DNA arm segment is preferably 5 to 9 nucleotides long, and more preferably 6 to 8 nucleotides long, and each primer is about 10 to 20 nucleotides long, and more preferably 12 to 18 nucleotides long. However, in some instances, longer or shorter sequences are also suitable. In this case, the polynucleotide's DNA arm segments may comprise one or more C or G nucleotide(s) at the 5' terminus and a similar number of complementary nucleotide at the 3' terminus. The pairing of these nucleotide(s) provides strong hybridization and prevents the sliding of the DNA segments with respect to one another. A preferred number of C or G nucleotides at the 5' terminus of the polynucleotide's (or fluorescent beacon's) arm segments is about 1 to 8, and more preferably about 3 to 5 C or G nucleotides, and a similar number of complementary nucleotide at the 3' terminus of the extension arms. In addition, the arm segments can further comprise one or more A or T nucleotide vicinal to the one or more C or G nucleotide(s) at the 5' terminus in a similar number of complementary nucleotides vicinal or next to the one or more G or C nucleotide(s) at the 3' terminus. As may be surmised, the addition of A:T pairs next to the G:C pairs further reinforces the strength of the hybridization exhibited by the extension arms. The number of A or T nucleotides vicinal to the C or G nucleotides at the 5' terminus of the extension arms is preferably 1 to 4, and more preferably 2 to 3. Consequently, the number of complementary nucleotides next to the G or C nucleotides at the 3' terminus is also 1 to 4, and more preferably 2 to 3.

The reagents, including enzymes, which may be utilized in the polymerized chain reaction (PCR) are known in the art. See, for example, U.S. Pat. Nos. 5,210,015; 4,683,195; 4,683,202; 4,965,188; 4,800,159; and 4,889,818, the relevant portions of which are incorporated by reference. However, preferred cycling conditions for this reaction are about 1 to 30 cycles, more preferably 5 to 20 cycles, and still more preferably 10 to 15 cycles, at alternating between temperatures of about (1) 58 to about 95° C.: to (2) about 58 to about 95° C. Some of the more preferred temperature combinations being about 95: about 58° C., about 58: about 74° C. and about 74: about 95° C. However, other combinations are also suitable. A preferred amount of beacon DNA is approximately the same as or about the concentration of both primer DNAs used. However, other proportions may also be utilized as an artisan would know. See, for example, the US Patents listed above.

In another preferred embodiment, the DNA internal segment of the polynucleotide binds to universal or conserved nucleic acid sequences of a large number of viruses and microorganisms, including bacteria, yeast, molds and protista. In still a more preferred embodiment, the internal DNA segment comprises a sequence which hybridizes to, and may be complementary to a contiguous specific universal bacterial nucleic acid sequence and, therefore, it hybridizes to all classes of bacteria. By means of example, a bacteria-specific nucleic acid sequence comprises 5'-ATCTTCG-3' (SEQ. ID NO: 115), and the internal DNA segment comprises a complementary sequence thereto, i.e. 5'-CGAAGAT-3' (SEQ. ID NO: 116). Other sequences, however, may also be utilized. In one preferred embodiment, both the internal DNA segment and the extension arms are formed by a sequence which is complementary to a contiguous bacteria-specific bacterial nucleic acid sequence. By means of example, the nucleic acid sequence of the polynucleotide (or beacon) may comprise 5'-CCACCGACGAAGATTCGGTGG-3' (SEQ. ID NO: 117). Others, however, are also suitable.

In yet another embodiment, the polynucleotide (or fluorescent beacon) may be a specific probe for a class of microorganisms, for a specific species or for a group of species, depending on the DNA internal segment chosen. Examples of all of the above are provided in the Tables below.

The present method is similarly applicable to the detection of viruses by implementing the method described above. Similarly, nucleic acid sequences which are specific for yeast may be utilized to design primers which will bind upstream and downstream from the sequences to amplify the yeast nucleic acid sequence, and to manufacture a polynucleotide (or fluorescent beacon) by selecting a complementary DNA sequence which includes the DNA internal segment and the DNA arm segments and may additionally have the A:T and C:G termini. Alternatively, the DNA internal segment may comprise a sequence complementary to the yeast nucleic acid and the arm segments may be "false arms" constituted by complementary strings of A, T, C and G for form A:T and C:G pairs. This may also be attained with specific sequences for molds and/or protista in the same manner.

Various universal and specific microbial and viral nucleic acid sequences, primers, and DNA sequences suitable for use in the polynucleotide (or fluorescent beacon) in accordance with the present invention are provided below. However, the practice of this invention is not limited to the sequences described herein but, in addition, may be practiced with other universal nucleic acid sequences or sequences specific for either a species or a class of microorganism or virus. In another embodiment of the invention, whether or not a sample is sterile or has microbial and/or viral contamination may be determined by using a "pre-mix" of reagents with which a sample is mixed, and a specialized instrument for detecting fluorescence. This embodiment may be performed in a period of time as short as about 10 minutes. In this embodiment, the reagent "pre-mix" may comprise two primers and a fluorescent molecular probe or beacon, to which are added the sample and the PCR reagents, e.g. enzyme.

The necessary elements for implementing this technology are provided as a kit for detecting a microbe and/or virus. The detection kit comprises in separate containers primers binding to sequences up-stream and down-stream to a universal or specific microbial and/or viral nucleic acid sequence; and optionally, a polynucleotide comprising a DNA internal segment that is hybridizably complementary to at least a portion of the universal or specific nucleic acid sequence; and a first and a second DNA arm segment adjoining the DNA internal segment, the first DNA arm segment ending in a 5' terminus and the second DNA arm segment ending in a 3' terminus, the arms segments comprising nucleotide sequences such that they are hybridizably complementary to one another. Optionally, the terminus of one arm segment is operatively connected to a fluorogen and the terminus of the other arm segment is operatively connected to a quencher, such that the polynucleotide comprises a "fluorescent beacon."

Also included in the kit are instructions for use of the kit to detect the presence of a microbe(s) or virus(es).

As described above, in one preferred embodiment the DNA internal segment and the two arm segments of the polynucleotide (or fluorescent beacon) are fully complementary to a contiguous universal microbial nucleic acid sequence. Preferably, the internal DNA segment is about 7 to about 19 nucleotide long, each extension arm is about 5 to about 9 nucleotides long, and each primer is about 10 to about 20 nucleotides long. In another embodiment, only the DNA internal (or probe) segment of the polynucleotide (or fluorescent beacon) is complementary to a universal microbial nucleic acid sequence. Although the DNA arm segments are complementary to one another, one or both of them can be unrelated to the universal microbial nucleic acid sequence. In the latter case, although the length of the different parts of the fluorogenic beacon are similar to the one described above, the arm segments preferably comprise at least one C or G nucleotide at the 5' terminus in a similar number of complementary nucleotide at the 3' terminus, which permits the formation of G:C pairs by hybridization. More preferably the arm segments comprise about 1 to 8 C or G nucleotide at the 5' terminus and I to 8 complementary nucleotide(s) at the 3' terminus. Still more preferably 2 to 6 G or C nucleotide(s) at the 5' nucleotide at the 5' terminus and 2 to 6 complementary nucleotide at the 3' terminus. In addition, the DNA arm segments may further comprise one or more A or T nucleotide(s) vicinal or next to the C or G nucleotide at the 5' terminus, and the other arm comprises a similar number of complementary nucleotides vicinal to the G or C nucleotide(s) at the 3' terminus, thereby reinforcing the strength of the double stranded DNA portion. Preferably, the A or T nucleotide segments comprises 1 to 4 nucleotide (s) vicinal to the C or G nucleotide(s) at the 5' terminus and the other arm segment comprises 1 to 4 complementary nucleotide(s) to the A or T, which are placed vicinal or next to the G or C nucleotide(s) at the 3' terminus. In another embodiment, the DNA internal segment is complementary to a bacteria-specific nucleic acid sequence. Although the DNA arm segments are still complementary to one another, one or both can be unrelated to the bacteria-specific nucleic acid sequence. In this case, one of the DNA arm segments of the polynucleotide (or beacon) comprises at least one and up to 8 C or G nucleotide(s) at the 5' terminus and the other arm segment comprises a similar number of complementary nucleotides at the 3' terminus. As already explained above, the DNA arm segments can additionally comprise 1 to 4 A or T nucleotides(s) next to the C or G nucleotide(s) at the 5' terminus and the other arm comprises 1 to 4 complementary nucleotide vicinal to the one or more G or C nucleotide(s) at the 3' terminus. Examples of sequences suitable for use as arm segments are 5'- GCTAG -3' (SEQ. ID NO: 11 8) and 5'-CTAGC-3' (SEQ. ID NO: 119), although many others are also suitable. By means of example, the internal DNA segment of the fluorogenic beacon may be complementary to a conserved region of a small ribosomal RNA (rRNA) operon, a first primer may comprise 5'-GCTAAGGTCCCAAAGT-3' (SEQ. ID NO: 120), and a second primer may comprise 5'-AGAACGCTCTCCTACC-3' (SEQ. ID NO: 121). Another example is that where the DNA internal segment of the polynucleotide (or fluorescent beacon) is complementary to a conserved region of the small rRNA operon encoding a 23S rRNA, wherein the internal DNA segment of the beacon is complementary to the sequence 5'- CTTAGAAGCAG -3'-3' (SEQ. ID NO: 122). The oligonucleotide primers of the present invention, useful in the present kit, are optionally connected at their 5'-ends to a fluorogen, e.g., fluoroscein, or at their 3'-ends to a quencher, e.g., dabcyl.

The universal or specific nucleic acid sequence may be selected, and the complementary internal DNA segment of the polynucleotide (or fluorescent beacon) designed, for microorganisms such as bacteria, yeast, mold or protista. The DNA internal segment may be complementary to a contiguous nucleic acid sequence which is universal to a class of microbes as opposed to all microbes. Examples of these are provided below. The DNA internal segment moreover, may be complementary to a contiguous nucleic acid sequence which is virus-specific or specific to a class of viruses. When the kit is applied to the detection of bacteria at large, the DNA internal segment can comprise a sequence that is complementary to a contiguous universal bacteria-specific bacterial nucleic acid sequence, such as 5'-CCACCGAATCTTCGTCGGTGG-3' (SEQ ID NO: 144), or its complement, although others are also suitable. In another embodiment both the DNA internal segment and the arm segments comprise a nucleic acid sequence, such as 5-CCACCGACGACGAAGATTCGGTGG-3' (SEQ. ID. NO.: 117); although others may also utilized. Where the present technology is applied to the detection of virus, the DNA internal segment or both the DNA internal segment and the arm segments may be complementary to a nucleic acid which is conserved in all viruses, conserved over a class of viruses or a virus-specific nucleic acid sequence.

Any fluorogen (or fluorogenic agent) known in the art may be utilized with the present technology. Particularly suitable are pico green, fluorescein, edans, and the like. However, others may also be utilized. Similarly, any quencher known in the art is suitable for use herein. By means of example, dabcyl is suitable for the present purpose, although others may be utilized. Both the fluorogenic agent and the quencher are linked to the DNA portion of the fluorogenic beacon by $C_6$-thio or $C_7$-amino linkers known in the art, and the linkage is conducted as is known in the art. See, for example, Columns 1–2, page 1143, Schofield et al., Appl. & Ennison. Microbiol. 63(3):1143 (1997); Tyagi & Kramer, Nature Biotech. 14:303 (1996), the text of which is incorporated herein by reference.

In one preferred embodiment of the present kit, the primers and the polynucleotide (or fluorescent beacon) are pre-mixed in bulk, or in unitary amounts and provided in unitary form. The kit may also comprise one or more controls such as universal microbial and viral nucleic acid sequences and/or microbe-specific and viral-specific nucleic acid sequences. The controls may be provided as a panel for all microorganisms and/or viruses as well as different classes or specific species of bacteria or viruses.

In a preferred embodiment of this invention, the DNA primers comprise universal DNA oligomers, which are suitable for amplifying all eukaryotic and prokaryotic microorganisms, including bacteria, mold, yeast and/or protista, or viruses. In a broadly encompassing embodiment of the method of this invention, a predetermined volume of sample is mixed with the primers and other PCR reagents, a PCR reaction conducted, a fluorogenic beacon added and fluorescence detected.

The kit may further comprise PCR reagents. A most preferred embodiment of the kit, comprises a “pre-mix” of reagents, and instructions for DNA amplification and for conducting a PCR under specific cycling conditions. As already indicated, the kit of the invention may be a kit for generally assessing the presence or absence of microorganisms, e.g., bacteria, in a sample or may be custom tailored for the detection of specific organisms, such as any desired bacterium. An embodiment of the method and kit of the invention suitable for the determination of bacterial contamination in general may comprise a bacteria-specific nucleic acid sequence and its corresponding primers. The inventor has found that when a bacteria-specific sequence and its primers are subjected to PCR under certain conditions, the method of the invention provides high specificity for the bacterial genus. The universal microbial and/or viral nucleic acid sequence is preferably provided in the form of a stem-loop structure. However, the nucleic acid sequence need not be in this form. The nucleic acid target sequence may be in linear and/or circular form, as well. The polynucleotide (or fluorescent beacon), however, must generally conform to a stem-loop structure, and must comprise at least an DNA internal segment which is complementary to the target sequence. See, Tyagi and Kramer, Nature Biotech. 14:303 (1996). If the microbial and/or viral target sequence is not in the form of a stem-loop structure, the polynucleotide (or fluorescent beacon) must contain additional nucleotides at either, or both, end(s) of the complementary region to form a "false stem-loop" (arm segments). See, Schofield et al., App. & Environmental Microbiol. 63(3):1143 (1997).

A preferred "false stem-loop" comprises one or more of G:C, C:G, T:A, A:T, G:C, b/e last and/or C:G 1st, and the false stem-loop sequence is generally about 3 to about 51 nucleotides long, and preferably about 7 to about 31, and more preferably about 12 to about 28 nucleotides long. Most preferred are false stem-loop segments about 13, about 15, about 17, about 19 and about 21 nucleotides long. However, other lengths are also suitable. The nucleotide segments may also comprise even numbers of nucleotide. However, odd-number nucleotide segments are preferred because they provide a trans-hybridization configuration which yields greater fluorescence. Where a preferred false stem structure may not attainable, the nucleotide segment of the polynucleotide (or beacon) must comprise at least about 2 G:C nucleotide pairs positioned at the termini (linker arm ends), and up-stream from it, preferably immediately up-stream, at least one T:A nucleotide pair(s) to prevent slipping in the stem hybrid (G:C,C:G, T:A, . . . ) for proper attachment of the polynucleotide's (or beacon's) arms where in single stranded form. This sequence is generally followed by at least about 1, preferably about 2 more complementary base pairs, and up to about 8 complementary base pairs, preferably G:C pairs, to require a high enough melting temperature for the stem hybrid structure to remain stable at ambient temperature.

A preferred polynucleotide (or beacon molecule) for the universal detection of bacteria comprises 5'-GGTGGCTGCTTCTAAGCCACC-3' (SEQ. ID. NO: 141) or analogues thereof which hybridize under the following conditions, and preferably under stringent conditions, to a DNA sequence complementary thereto. Other polynucleotide DNAs (or beacon molecules) are also suitable and may be utilized in conjunction with this invention. Such molecules are designed to be complementary to conserved regions in the small rRNA operon encoding the 23S rRNA. Its corresponding primers comprise segments 5'-GCTAAGGTCCCAAAGT-3' (SEQ. ID. NO. 120), and 5'-AGAACGCTCTCCTACC-3' (SEQ. ID. NO. 121). These sequences were deduced from highly conserved regions of the rRNA operon encoding 23s rRNA. Other universal probes or internal DNA segments suitable for use with this invention are those which have a sequence complementary to the target nucleic acid sequences described by Hill (1996), supra, and include highly conserved sequences such as a 16S rRNA, an rRNA spacer, a 16S rDNA, a 16S DNA, which are listed in Table 2 of the publication. Hill (1996), supra also provides in Table 2 sequences specific for individual microorganism targets, including *Aeromonas hydrophila* aer, Brucella spp. 1 6S rDNA, Brucella spp. Putative OMP, *Campylobacterjejuni* flaA, *E. coli* flaA, *C.jejuni* 16S rRNA, *E. coli* 16S rRNA, C. Lari 16S rRNA, Clostridia 16S rDNA (2 sequences), *Clostridium botulinum* Neurotoxin A, *Clostridium botulinum* Neurotoxin B, etc. Some of the sequences encompassed by the group to which the invention is applicable are listed below. This, however, is not an all inclusive list of known highly conserved and specific sequences for microbial and viral targets.

TABLE 1

Examples of Highly Conserved Target Sequences

| Organism | Target | Size (bp) | Primer Sequences | Ann. Temp. (° C.) | Cycles |
|---|---|---|---|---|---|
| All Bacteria | 16S rRNA | 408 | CAGCMGCCGCGGTAATWC<br>CCGTCAATTCMTTTRAGTTT<br>(SEQ. ID NO: 1) | 50 | 30 |
| All Bacteria | rRNA Spacer | Varies | GAAGTCGTAACAAGG<br>CAAGGCATCCACCGT<br>(SEQ. ID NO: 2) | 55 | 25 |
| All Bacteria | 16S rDNA | –335 | GAGTTTGATCCTGGCUCA<br>(SEQ. ID NO: 3) | 60 | 35 |

Table 2 below shows several sequences of molecular beacons and indicates whether the sequences are universal or specific for a certain organism. See, Hill, W. E., Crit. Rev. Food Sci. & Nutrition 36(1 & 2):123 (1996).

TABLE 2

Examples of Molecular Beacon Sequences

| Organism | Molecular Beacon Sequence |
|---|---|
| Universal | 5'-CCTGCACGGGCGGTGTGTACGCAGG-3'<br>(SEQ. ID NO: 123) |
| *Ruminococcus albus* 8 | 5'-CCCCCGTCATGCGGCTTCGTTATGGGGG-3'<br>(SEQ. ID NO: 124) |
| *Fibrobacter succinogenes* S85 | 5'-GCTGCCTGCCCCTGAACTATCCAAGAGGCAGC-3'<br>(SEQ. ID NO: 125) |

Examples of sequences for organism specific targets and the respective organism are provided in Table 3 below.

TABLE 3

Examples of Specific Target Sequences

| Organism | Target (bp) | Size | Primer Sequences | Ann. Temp. (° C.) | Cycles |
|---|---|---|---|---|---|
| All Bacteria | 16S rRNA | 408 | CAGCMGCCGCGGTAATWC CCGTCAATTCMTTTRAGTTT(SEQ ID NO:1) | 50 | 30 |
| All Bacteria | rRNA spacer | Variable | GAAGTCGTAACAAGG CAAGGCATCCACCGT (SEQ ID NO:2) | 55 | 25 |
| All Bacteria | 16S rDNA | ~335 | GAGTTTGATCCTGGCUCA CTGCTGCCTCCCGTA (SEQ ID NO:3) | 60 | 35 |
| Eubacteria | 16S DNA | ~1500 | AGAGTTTGATCCTGGCTCAG AAGGAGGTGATCCAGCCGCA (SEQ ID NO:4) | 55<br>42 | 26<br>25–30 |
| *Aeromonas hydrophila* | aer | 209 | CCAAGGGGTCTGTGGCGACA TTTCACCGGTAACAGGATTG (SEQ ID NO:5) | 55 | 30 |
| Brucella spp. | 16S rDNA | 801 | TGCTAATACCGTATGTGCTT TAACCGCGACCGGGATGTCAA (SEQ ID NO:6) | 50 | ? |
| Brucella spp. | Putative OMP | 635 | Sequences not reported | 60 | 50 |
| *Campylobacter jejuni* and *Campylobacter coli* | flaA | 560 | ATGGGATTTCGTATTAAC GAACTTGAACCGATTTG (SEQ ID NO:7) | 37 | 25 |
| *Campylobacter jejuni, Campylobacter coli, Campylobacter lari* | 16S rRNA | 426 | ACCTTGTTACGACTTCACCCCA GAGAGTTTGATCCTGGCTCAG (SEQ ID NO:8) | 52 | 40 |
| Clostridium spp. | 16S rRNA | ~1371 | GATCCTGGCTCAG GACGGGCGGTGTGTACAA (SEQ ID NO:9) | 50 | 40 |
| Clostridium spp. | 16S rDNA | ~502 | AAACTCAAATGAATTGACGG GACGGGCGGTGTGTACAA (SEQ ID NO:10) | 50 | 40 |
| *Clostridium botulinum* | Neurotoxin B | ~1500 | GATGGAACCACCATTTGCWAG WACATCWATACAWATTCCTGG (SEQ ID NO:11) | 37 | 25 |
| *Clostridium botulinum* | Neurotoxin A | ~1340 | GATCCTGTAAATGGTGTTG CAAGTCCCAATTATTATAACTTTG AT (SEQ ID NO:12) | 55 | 35 |
| Coliform bacteria | lacZ | ? | TGAAAGCTGGCTACAGGAAGGCC GGTTTATGCAGCAACGGACGTCA (SEQ ID NO:13) | 60 | 30 |
| *Entamoeba histolytica* | cEH-P1 clone | 482 | GCAACTACTGTTAGTTA CCTCCAAGATATGTTTTAAC (SEQ ID NO:14) | 42 | 25–35 |
| *Escherichia coli* | afa | 750 | GCTGGGCAGCAAACTGATAACTC TCCATCAAGCTGTTTGTTCGTCCG CCG (SEQ ID NO:15) | 65 | 25 |
| *Escherichia coli* | elt | 275 | TTACGGCGTTACTATCCTCTCTA GGTCTCGGTCAGATATGTGATTC (SEQ ID NO:16) | 55 | 30 |
| *Escherichia coli* | eltB | 195 | CCTCTCTATATGCACACGGAGCTC CCAGCTATATTGTTGACTGCCCGG GACTTCGACC (SEQ ID NO:17) | 54 | 40 |
| *Escherichia coli* | sltllva | 490 | TGTGTTTGCTTGTCTTCAGC ATGCGCGGGGTCATGGAACGT (SEQ ID NO:18) | 55 | 30 |
| *Escherichia coli* | elt | 750 | GGCGACACATTATACCGTGC CCGAATTCTGTTATATATGTC (SEQ ID NO:19) | 43 | 26 |
| *Escherichia coli* | est | 186 | TCTGTATTGTCTTTTTCACC TTAATAGCACCCGGTACAAGC (SEQ ID NO:20) | 43 | 26 |
| *Escherichia coli* | estA | 175 | TTTTTCTGTATTTTCTTTIICII CTTIIITCAGGCAGGATTACAA CAIAITTCACAGC (SEQ ID NO:21) | 55 | 30 |
| *Escherichia coli* | malB | 595 | TCGCCACACGCTGACGCTGAC CATTACATGACCTCGCTTTAG TTCACAGA (SEQ ID NO:22) | 60, 65, 70 | 65 |
| *Escherichia coli* | papC | 328 | GACGGCTGTACTGCAGGGTGT | 65 | 25 |

TABLE 3-continued

Examples of Specific Target Sequences

| Organism | Target (bp) | Size | Primer Sequences | Ann. Temp. (° C.) | Cycles |
|---|---|---|---|---|---|
| | | | GGCGATATCCTTTCTGCAGGG ATGCAATA (SEQ ID NO:23) | | |
| *Escherichia coli* | | 410 | CTCCGGAGAACTGGGTGCATC TTACCGGAGGAGTAATTACA AACCTGGCA (SEQ ID NO:24) | 65 | 25 |
| *Escherichia coli* | sltA | 140 | ACCCTGTAAACGAAGTTTGCG ATCTCATGCGACTACTTGAC (SEQ ID NO:25) | 55 | 30 |
| *Escherichia coli* | STI (a and b) | ? | TTAATAGCACCCGGTACAAGC AGGCCTGACTCTTCAAAAGA GAAAATTAC (SEQ ID NO:26) | 58 | 35 |
| *Escherichia coli* | toxA | 110 | CCGGTATTACAGAAATCTGA GTGCATGATGAATCCAGGGT (SEQ ID NO:27) | 55 | 35 |
| *Escherichia coli* | toxB (eltB) | 298 | CAGTCTATTACAGAACTATG CCATACTGATTGCCGCAATTG (SEQ ID NO:28) | 30 | 25 |
| *Escherichia coli* | stx/slt-IA | 680 | GACAGGATTTGTTAACAGG TTCCAGTTACACAATCAGGCC (SEQ ID NO:29) | 55 | 30 |
| *Escherichia coli* | sltl | 614 | ACACTGGATGATCTCAGTGG CTGAATCCCCCTCCATTATG (SEQ ID NO:30) | 60 | 35 |
| *Escherichia coli* | sltll | 779 | CCATGACAACGGACAGCAGT T CCTGTCAACTGAGCACTTTG (SEQ ID NO:31) | 60 | 35 |
| *Escherichia coli* | SLT-IA | 370 | AAATCGCCATTCGTTGACTAC TTCT TGCCATTCTGGCAACTCGCGA TGCA (SEQ ID NO:32) | 60 | 35 |
| *Escherichia coli* | SLT-IIA | 283 | CAGTCGTCACTCACTGGTTTC ATCA GGATATTCTCCCCACTCTGAC ACC (SEQ ID NO:33) | 60 | 35 |
| *Escherichia coli* | SLTIA, SLTIIA | 224, 227 | TTTACGATAGACTTTTCGAC CACATATAAATTATTTCGCTC (SEQ ID NO:34) | 43 | 30 |
| *Escherichia coli* | slt-II (vtx2) | 285 | AAGAAGATGTTTATGGCGGT CACGAATCAGGTTATGCCTC (SEQ ID NO:35) | 55 | ? |
| *Escherichia coli* | vtx2 | 385 | CATTCACAGTAAAAGTGGCC GGGTGCCTCCCGGTGAGTTC (SEQ ID NO:36) | 45 | ? |
| *Escherichia coli*, Salmonella spp. and Shigella spp. | lamB | 346 | CTGATCGAATGGCTGCCAGGC TCCCAACCAGACGATAGTTAT CACGCA (SEQ ID NO:37) | 60 | 30 |
| *Escherichia coli* and Shigella spp. | Putative inv | 760 | TAATACTCCTGAACGGCG TTAGGTGTCGGCTTTTCTG (SEQ ID NO:38) | 55–65 | 30 |
| *Escherichia coli* and Shigella spp. | stx, sltl | 130 | GAAGAGTCCGTGGGATTACG AGCGATGCAGCTATTAATAA (SEQ ID NO:39) | 55 | 30 |
| *Escherichia coli* and Shigella spp. | uidA | 166 | TATGGAATTTCGCCGATTTT TGTTTGCCTCCCTGCTGCGG (SEQ ID NO:40) | 50 | 25 |
| *Escherichia coli* and Shigella spp. | uidR | 153 | TGTTACGTCCTGTAGAAAGCCC AAACTGCCTGGCACAGCAATT (SEQ ID NO:41) | 59 | 25 |
| | uidR | 154 | TGTTACGTCCTGTAGAAAGCCC AAAACTGCCTGGCACAGCAATT (SEQ ID NO:145) | 60 | (30) |
| *Shigella dysenteriae* | ail<br>ial | 320 | CTGGATGGTATGGTGAGG<br>GGAGGCCAACAATTATTTCC (SEQ ID NO:42) | 43<br>43 | 26<br>25–30 |
| *Shigella dysenteriae* | ipaH | 700 | GTTCCTTGACCGCCTTTCCGATAC GCCGGTCAGCCACCCTC (SEQ ID NO:43) | 60 | 35 |
| Giardia spp. | Giardin | 171 | AAGTGCGTCAACGAGCAGCT TTAGTGCTTTGTGACCATCGA (SEQ ID NO:44) | 60 | 25 |
| *Giardia duodenalis* | Giardin | 218 | CATAACGACGCCATCGCGGCTCT CAGGAA TTTGTGAGCGCTTCTGTCGTGGCA | 60 | 25 |

TABLE 3-continued

Examples of Specific Target Sequences

| Organism | Target (bp) | Size | Primer Sequences | Ann. Temp. (° C.) | Cycles |
|---|---|---|---|---|---|
| | | | GCGCTAA (SEQ ID NO:45) | | |
| *Helicobacter pylori* | 16S rDNA | 109 | CTGGAGAGACTAACGGGTGG ATTACTGACGCTGATTCTGC (SEQ ID NO:46) | 60 | 40 |
| *Helicobacter pylori* | 16S rRNA | ~500 | TGGCAATCAGCGTCAGGTAATG GCTAAGAGATCAGCCTATGTCC (SEQ ID NO:47) | 55 | 40 |
| *Helicobacter pylori* | ureA | 412 | GCCAATGGTAAATTAGTT CTCCTTAATTGTTTTTAC (SEQ ID NO:48) | ? | 26 |
| *Helicobacter pylori* | ureA and ureB | 2396 | AGGAGGATGAGATGA ACTTTATTGGCTGGT (SEQ ID NO:49) | 50 | 30 |
| Listeria spp. | 16S rDNA | 938 | CAGCMGCCGCGGTAATWC CTCCATAAAGGTGACCCT (SEQ ID NO:50) | 50 | 30 |
| Listeria spp. | iap | 1454 | ATGAATATGAAAAAAGCAAC TTATACGCGACCGAAGCCAA (SEQ ID NO:51) | 50 | 30 |
| *Listeria monocytogenes* and *Listeria innocua* | iap | 1448 | GCTACAGCTGGGATTGCGGT TTATACGCGACCGAAGCCAA (SEQ ID NO:52) | 55 | 40 |
| *Listeria innocua* | iap | ~870 | ACTAGCACTCCAGTTGTTAA TTATACGCGACCGAAGCCAA (SEQ ID NO:53) | 62 | 30 |
| *Listeria invanovii, Listeria seeligeri,* and *Listeria welshimeri* | iap | 1243 | TTACTGAGGTAGCRAGC TTATACGCGACCGAAGCCAA (SEQ ID NO:54) | 58 | 30 |
| *Listeria monocytogenes* | 16S rRNA | 70 | CACGTGCTACAATGGATAG AGAATAGTTTTATGGGATTAG (SEQ ID NO:55) | 48 | 40 |
| *Listeria monocylogenes* | hylA | 417 | CATCGACGGCAACCTCGGAGA ATACAATTACCGTTCTCCACCATT C (SEQ ID NO:56) | 62 | 30 |
| *Listeria monocytogenes* | hylA | 520 | AACCTATCCAGGTGCTC CGCCACACTTGAGATAT (SEQ ID NO:57) | 60 | 35 |
| *Listeria monocytogenes* | hlyA | 174 | GCATCTGCATTCAATAAAGA TGTCACTGCATCTCCGTGGT (SEQ ID NO:58) | 56 | 30 |
| *Listeria monocytogenes* | hlyA | 234 | CGGAGGTTCCGCAAAAGATG CCTCCAGAGTGATCGATGTT (SEQ ID NO:59) | 50, 55 56 | 30 30 |
| *Listeria monocytogenes* | hlyA | 606 | Sequence not reported | 51 | 30 |
| *Listeria monocytogenes* | hlyA | 685[c] | CCTAAGACGCCAATCGAA AAGCGCTTGCAACTGCTC (SEQ ID NO:60) | 50 | 30 |
| *Listeria monocytogenes* | hlyA | 702 | CCTAAGACGCCAATCGAA AAGCGCTTGCAACTGCTC (SEQ ID NO:61) | 50 | 30 |
| *Listeria monocytogenes* | hlyA | 234 | ATTGCGAAATTTGGTACAGC ACTTGAGATATATGCAGGAG (SEQ ID NO:62) | 55 | 30 |
| *Listeria monocytogenes* | downstream from hlyA | ? | Sequences not reported | 55 | 30 |
| *Listeria monocytogenes* | iap (msp) | 131 | ACAAGCTGCACCTGTTGCAG TGACAGCGTGTGTAGTAGCA (SEQ ID NO:63) | 55 | 30 |
| *Listeria monocytogenes* | iap | 544 | CAAGCAACTACACCTGCGCC GAACCTTGTTAGCATTCGT (SEQ ID NO:64) | 50 | 30 |
| *Listeria monocytogenes* | msp (iap) | 593 | ACAAGCTGCACCTGTTGCAG GAACCTTGTTAGCATTCGT (SEQ ID NO:65) | 50 | 30 |
| *Listeria monocytogenes* | iap | 287 | CGAATCTAACGGCTGGCACA GCCCAAATAGTGTCACCGCT (SEQ ID NO:66) | 50 | 30 |
| *Listeria monocytogenes* | iap | 380+/−40[d] | CAAACTGCTAACACAGCTACT GCACTTGAATTGCTGTTATTG | 65 | 35 |

TABLE 3-continued

Examples of Specific Target Sequences

| Organism | Target (bp) | Size | Primer Sequences | Ann. Temp. (° C.) | Cycles |
|---|---|---|---|---|---|
| | | | (SEQ ID NO:67) | | |
| *Listeria monocytogenes* | Dth-18 | 326 | CCGGGAGCTGCTAAAGCGGT GCCAAACCACCGAAAATACC (SEQ ID NO:68) | 54 | 30 |
| *Listeria monocytogenes* | Dth-18 | 122 | GAAGCACCTTTTGACGAAGC GCTGGTGCTACAGGTGTTTC (SEQ ID NO:69) | 54 | 30 |
| *Listeria monocytogenes* | ImaA | 257 | AACAAGGTCTAACTGTAAAC ACTATAGTCAGCTACAATTG (SEQ ID NO:70) | 55 | 30 |
| Salmonella spp. | DNA rep. ori. | 163 | TTATTAGGATCGCGCCAGGC AAAGAATAACCGTTGTTCAC (SEQ ID NO:71) | 50 | 35 |
| *Staphylococcus aureus* | entA | 120 | TTGGAAACGGTTAAACGAA GAACCTTCCCATCAAAAACA (SEQ ID NO:72) | 55 | ? |
| *Staphylococcus aureus* | entB | 478 | TCGCATCAAACTGACAAACG GCAGGTACTCTATAAGTGCC (SEQ ID NO:73) | 55 | ? |
| *Staphylococcus aureus* | entB | 593 | GAGAGTCAACCAGATCCTAAACC AGATACCAAAAGCTATTCTCATTT TCT (SEQ ID NO:74) | 50 | 50 |
| *Staphylococcus aureus* | entC1 | 801 | ATGAATAAGAGTCGATTTATTTC ATTTATCCATTCTTTGTTGTAAGG TGG (SEQ ID NO:75) | 50 | 50 |
| *Staphylococcus aureus* | entC1 | 631 | ACACCCAACGTATTAGCAGAGAG CCCCTGGTGCAGGCATCATATCA TACC (SEQ ID NO:76) | 50 | 50 |
| *Staphylococcus aureus* | entC1 | 257 | GACATAAAAGCTAGGAATTT AAATCGGATTAACATTATCC (SEQ ID NO:77) | 55 | ? |
| *Staphylococcus aureus* | entD | 317 | CTAGTTTGGTAATATCTCCT TAATGCTATATCTTATAGGG (SEQ ID NO:78) | 55 | ? |
| *Staphylococcus aureus* | entE | 170 | TAGATAAAGTTAAAACAAGC TAACTTACCGTGGACCCTTC (SEQ ID NO:79) | 55 | ? |
| *Staphylococcus aureus* | tst | 186[e] | TTCACTATTTGTAAAAGTGTCAGA CCCCACTTACTAATGAATTTTTTT ATCGTAAGCCCTT (SEQ ID NO:80) | 55 | 40 |
| *Staphylococcus aureus* | tst | 350 | ATGGCAGCATCAGCTTGATA TTTCCAATAACCACCCGTTT (SEQ ID NO:81) | 55 | ? |
| *Staphylococcus aureus* | eat | 119 | CTAGTGCATTTGTTATTCAA TGCATTGACACCATAGTACT (SEQ ID NO:82) | 55 | ? |
| *Staphylococcus aureus* | etb | 200 | ACGGCTATATACATTCAATT TCCATCGATAATATACCTAA (SEQ ID NO:83) | 55 | ? |
| *Staphylococcus aureus* | nuc | 450 | AGTATATAGTGCAACTTCAACTA AAATCAGCGTTGTCTTCGCTCCAA ATA (SEQ ID NO:84) | 50 | 50 |
| *Staphylococcus aureus* | nuc | ~270 | GCGATTGATGGTGATACGGTT AGCCAAGCCTTGACGAACTAAAG C (SEQ ID NO:85) | 55 | 37 |
| *Vibrio cholerae* | ctx | 302 | CTCAGACGGGATTTGTTAGGCAC GTCTATCTCTGTAGCCCCTATTAC G (SEQ ID NO:86) | 60 | 30, 40 |
| *Vibrio cholerae* | ctx | 384 | CGGGCAGATTCTAGACCTTC GCACCCCAAATAGAACTCGA (SEQ ID NO:87) | 62 | 25 |
| *Vibrio cholerae* | ctxA | 564 | CGGGCAGATTCTAGACCTCCTGC GATGATCTTGGAGCATTCCCAC (SEQ ID NO:88) | 60 | 55 |
| *Vibrio cholerae* | ctxAB | 777 | TGAAATAAAGCAGTCAGGTGGTG ATTCTGCACACAAATCAG GGTATTCTGCACACAAATCAG (SEQ ID NO:89) | 55 | 25–35 |
| *Vibrio cholerae* | luxA | 350 | GGAAGCTTCCAATGATTCTAAGC TGGATGGGAATTCTCAGGCGTCC CTACTGGGTT (SEQ ID NO:90) | 55 | 25 |
| *Vibrio parahaemolyticus* | tdh | 648 | CTGTCCCTTTTCCTGCCCCCG GCTCTTAGCTGCGGCGGTGGT (SEQ ID NO:91) | 62 | 25 |

TABLE 3-continued

Examples of Specific Target Sequences

| Organism | Target (bp) | Size | Primer Sequences | Ann. Temp. (° C.) | Cycles |
|---|---|---|---|---|---|
| *Vibrio vulnificus* | Cytolysin | 388 | CGCCGCTCACTGGGGCACTGGCT GCCAGCCGTTAAGCGAACCACCC GC (SEQ ID NO:92) | 65 | 40, 50 |
| *Vibrio vulnificus* | Cytolysin | 519 | CCGCGGTACAGGTTGGCGCA CGCCACCCACTTTCGGGCC (SEQ ID NO:93) | 67–69 | 30 |
| *Yersinia enterocolitica* | ail | 273 | GAACTCGATGATAACTGGG GCAATTCAACCCACTTCAA (SEQ ID NO:94) | 65 | 35 |
| *Yersinia enterocolitica* | ail | 170 | ACTCGATGATAACTGGGGAG CCCCCAGTAATCCATAAAGG (SEQ ID NO:95) | 55 | 25, 30 |
| *Yersinia enterocolitica* | ail | 425 | TTAATGTGTACGCTGCGAGTG GGAGTATTCATATGAAGCGTC (SEQ ID NO:96) | 57 | 35 |
| *Yersinia enterocolitica* | inv | 359 | CTATTGGTTATGCGCAAAGC TGGAAGTGGGTTGAATTGCA (SEQ ID NO:97) | ? | ? |
| *Yersinia enterocolitica* | yst | 163 | AATGCTGTCTTCATTTGGAGC GCAACATACATCACAGCAAT C (SEQ ID NO:98) | 60 | 35 |
| *Yersinia enterocolitica* | yst | | AAAGATATTTTTGTTCTTGT GCAGCCAGCACACGCGGG (SEQ ID NO:99) | 43 | 30 |
| *Yersinia pseudotuberculosis* | inv | 295 | TAAGGGTACTATCGAGGCGG ACGTGAAATTAACCGTCACAC T (SEQ ID NO:100) | 55 | 25, 30 |
| Yersinia virulence plasmid | virF | 590 | TCATGGCAGAACAGCAGTCA GACTCATCTTACCATTAAGAA G (SEQ ID NO:101) | ? | ? |
| Yersinia virulence plasmid | virF | 590 | CATGGCAGAACAGCAGTCAG ACTCATCTTACCATTAAGAAG (SEQ ID NO:102) | 57 | 35 |
| Norwalk virus | Near 3' end | 456 | ATTGAGAGCCTCCGCGTG GGTGGCGAAGCGGCCCTC (SEQ ID NO:103) | 49 | 30–40 |
| Norwalk virus | pol | 470 | CTTGTTGGTTTGAGGCCATAT ATAAAAGTTGGCATGAACA (SEQ ID NO:104) | 55 | 40 |
| Norwalk virus | pol | 260 | CAAATTATGACAGAATCCTTC GAGAAATATGACATGGATTG C (SEQ ID NO:105) | 55 | 40 |
| Norwalk virus | IP | 224 | CACCACCATAAACAGGCTG AGCCTGATAGAGCATTCTTT (SEQ ID NO:106) | 50 | 40 |
| Rotavirus | vp7 | 1036 | GGCTTTAAAAGAGAGAATTTC CGTCTGG GGTCACATCATACAATTCCTA ATCTAAG (SEQ ID NO:107) | 42 | 25 |
| Rotavirus | Gottfried gene 4 seg. | ? | CCATATCAGCCAACGAGT TTACTACTTCTACATCAGGT (SEQ ID NO:108) | 42 | 30 |
| Rotavirus | OSU gene 4 seg. | ? | CATACCAACCAACCACTTTC TGATGTCATATTTACTGTGT (SEQ ID NO:109) | 42 | 30 |
| Rotavirus (group A) | near 5' end | 259 | GGCTTTTAAACGAAGTCTTC TCAACAATGCGTCTAAGTTCA CAG (SEQ ID NO:110) | 55 | 30 |
| Hepatitis A virus | VP1 | 302 | TCCCAGAGCTCCATTGAA CATTATTTCATGCTCCTCAG (SEQ ID NO:111) | 37 | 30 |
| Hepatitis A virus | VP3 | 207 | ACAGGTATACAAAGTCAG CTCCAGAATGATCTCC (SEQ ID NO:112) | 37 | 30 |
| Hepatitus A virus | VP3 | 207 | CTCCAGAATCATCTCC ACAGGTATACAAAGTCAG (SEQ ID NO:113) | 49 | 40 |
| | ? | ? | Sequences not reported | ? | 30 |
| Enteroviruses | Near 5' end | 154 | CCTCCGGCCCCTGAATGCGGC TAATTAACAGTGGATTCGTCG GT (SEQ ID NO:114) | 50 | 25, 50 |

Species specific primers and nucleic acid target sequences for *C. jejuni* are provided in Table 4 below. See, Day et al., Appl. Environ. Microbiol.: 1019 (March 1997).

TABLE 4

Further Species Specific Sequences

| Organism | Primers (5' to 3') | Target Sequence (5' to 3') |
|---|---|---|
| *Campylobacter jejuni* | | |
| " | AGTCAGCCAC (SEQ. ID NO: 126) | ATCGGGCTGTTATGATGATA (SEQ. ID NO: 127) |
| " | AATCGGGATG (SEQ. ID NO: 128) | ATCACTGGGGGAGCTAATAT (SEQ. ID NO: 129) |
| " | AGGGGTCTTG (SEQ. ID NO: 130) | TAAGGTTAAAGTTGTTGTGAATC (SEQ. ID NO: 131) |
| " | AGCCAGCGAA (SEQ. ID NO: 132) | CATATCCAGAGCCTCTGGAT (SEQ. ID NO: 133) |
| " | GAAACGGGTG (SEQ. ID NO: 134) | GTAGCCTCTTCATCGTCGTCTAA (SEQ. ID NO: 135) |
| " | GTGACGTAGG (SEQ. ID NO: 136) | CACCCGCTTTAACGCCAAGA (SEQ. ID NO: 137) |

The construction of the DNA beacon molecule, PCR reaction conditions, and sample preparation are detailed below. Briefly, generally known PCR reaction conditions are suitable. For example, a master pre-mix for a standard 50 μl reaction, although the volume may be reduced to as small as a 10 μl per reaction, may be as follows. 24 μl water free of nucleases, proteases, heavy metals and DNA/RNA may be mixed with 5 μl of a 2% PVPP aqueous solution (polyvinylpolypyrrolidone), 5 μl of 10×PCR buffer, e.g. 100 mM tris-HCl, pH 8.3, 500 mM KCl, 5 μl of 25 mM $MgCl_2$, 1.25 μl 50 ng/μl of each primer, 1 μl 10 mM of each dNTP, 2.5 μl of enzyme, e.g. AmpliTaq LD at a 1:5 dilution and 2 μl of DNA template preparation, as described below. The cycling parameters may be 30 sec. at 95 ° C., 30 sec. at 58° C. and 60 sec. at 74° C. This routine may be repeated 30–50 times depending on the sensitivity needed, which is generally empirically determined by the type of sample and sample preparation without undue experimentation.

The preparation of the sample is adapted empirically based on whether or not there are interfering substances in the sample, and what type of substances they are, as is known in the art. Once the proper sample preparation is attained, DNA extraction may be attained, for example, by simple boiling for 10 min prior to utilization of the sample as DNA template or target in the reaction. For example, to test for sterility of shelf stable commercially sterile pudding, the pudding may be diluted in ultrapure water 1:30 and boiled for 10 min before adding to the PCR pre-mix.

The fluorescent beacon is constructed by assembly of the separate parts, that is the nucleic acid and the fluorophore and quencher are synthesized separately and then bound by means of linkers, e.g. amino linkers, as is known in the art.

A large variety of microorganisms are involved in the contamination of, for example, food, cosmetics, medical supplies and fuids, blood products, intravenous solutions, and the like, among other commercial products. Examples of these are *E. coli*, Salmonella, Bacillus, Clostridium, Listeria, Pseudomonas, and many others including those listed above, all of which are promptly detected by the present technology, which is suitable for the standardized testing of products samples to determine their suitability for administration to or use in humans or animals. A necessarily incomplete list of microorganisms commonly present in foodstuffs is listed by Hill W. E., in Critical Rev. Food Sci. and Nutrition 36 (1 & 2): 123 (1996), along with other universal and specific bacterial primers and PCR cycling temperature pairs, the relevant pages thereof being incorporated herein by reference, e.g. pp. 140–146, among others. Other universal and specific sequences of internal DNA segments plus DNA arms including the 5' and 3' termini of the beacon are also provided by Schofield et al., Appl. and Environ. Microbiol. 63(3): 1143 (1997), the relevant sections of which are incorporated herein by reference, e.g., Tables 1 and 2, and the section on Cultivation of Bacteria, among others.

The reaction conditions for nucleic acid amplification may be custom tailored for the specific primers employed, and an artisan would know how to easily and quickly determine suitable conditions for specific applications. When the sample to be analyzed is suspected of containing a sufficient quantity of bacteria, generally a nucleic acid sequence about 100 and up to about 500 nucleotide long, and preferably up to about 200 base pairs long or even longer, may be amplified, and a polynucleotide DNA (or fluorescent beacon probe) designed so that it hybridizes to a portion of the DNA fragment. However, longer and smaller segments of nucleotide may also be utilized. When hybridized to a target, the amount of fluorescence emitted by polynucleotide plus fluorogenic reagents (or by a fluorescent beacon) is proportional to the amount of amplified nucleic acid present in the sample. The PCR conditions are generally set up so that the expected nucleic acid product comprises about 100 about 400 base pairs and contains, among other sequences, the target sequence for the complementary polynucleotide DNA internal segment (probe). However, other lengths are also suitable. The PCR may be conducted for as many cycles as necessary to obtain enough nucleic acid to bind the DNA beacon and obtain a linear fluorescent signal. In most cases up to about 30 PCR cycles are sufficient to produce enough nucleic acid target for the the DNA polynucleotide (or beacon) to bind to, and to produce sufficient fluorescence for observation with the naked eye after gel electrophoresis. A specialized instrument or fluorometer may be utilized for the measurement of fluorescence during the course of the reaction, and the display of typical response curves.

A sample may be assayed side-by-side with proper positive and negative controls, as is known in the art, and whether or not the sample has bacterial contamination may be conclusively determined in as short a time as 10 minutes. Positive controls may be conducted by following the same steps performed on the test sample but by adding to the medium a target nucleic acid sequence, e.g. naked DNA or bacteria, viruses, and the like. Negative controls are conducted in a manner similar to that of the test sample but contain no target nucleic acid.

This invention was described above in relation to the universal detection of microorganisms and/or viruses, and for the specific detection of a class of microorganism(s), e.g. bacteria, as well as for implementation with one beacon and two DNA primers. The invention is, however, not limited to either the described sequences, nor the number of polynucleotides (or fluorescent beacons) and primers. In fact, any combination of primer and polynucleotide (or beacon) sequences that are specific or universal for microorganisms and viruses, including yeast, molds, and the like, may be substituted and/or added to the nucleic acid target subjected to PCR. Examples of nucleic acid targets which may be utilized are those specific for a microorganism, or genus or class of microorganisms, such as a nucleic acid segment imparting a virulence trait, DNA sequences that are order-, class-, strain- and/or species-specific, such as those based on immunological identity, e.g. antigenic proteins or flagella. A partial list of DNA target probe sequences and their corresponding primers is provided by Hill, E. W. et al., Critical Rev. Food Sci. & Nutrition 36(182):123 (1996), the relevant text of which is incorporated herein by reference.

Similarly, nucleic acid targets and primers may also be utilized to design polynucleotides (or fluorescent beacons) which specifically hybridize to a single species of virus or microorganism, bacteria such as *E. coli*, Salmonella, Listeria, etc., viruses such as Rotavirus, Influenza, etc., among others. Thus, the assay and the kit of the invention may also be targeted to the determination of specific microorganisms and/or viruses. The kit of this invention along with a instructions to custom tailor and perform PCR may be applied for the intended use in conjunction with any commercially available thermocycler. One embodiment of this invention, therefore, provides a kit which contains a premixed composition comprising specific nucleic acid primers and beacon probes, which may carry a fluorescent molecule. Alternatively, the fluorogenic tag or beacon may be provided separately for attachment prior to use. The reaction mixture (pre-mix) is intended for direct mixing with a sample, and for practicing the present assay detecting the presence of microorganisms and viruses in as short a time as about 10 minutes after sample preparation. The kit of the invention may be pre-packaged in bulk for aliquoting by the user, or in unit form, as lyophilized or vitriculated form, in reaction vessels to ensure the stability of the components during shipping and storage. When in lyophilized or vitriculated form, the user may simply rehydrate the reaction ingredients in the vessel containing them or upon aliquoting, with a predetermined amount of sample preparation and conduct the detection step by placing the vessel in the fluorimeter.

The user of the kit of this invention need not be technically skilled to perform the assay provided here, to obtain accurate results. The present inventor has discovered and designed DNA segments for the universal detection of microorganisms, e.g. bacteria. Other DNA segments complementary to known nucleic acid sequences which have specificity for one or the other microorganism or virus may be designed and amplified by known PCR reactions for use with the present kit and assay. PCR reaction conditions are widely known in the art, and known and to-be-discovered universal and specific nucleic acid sequences, and primers, may be utilized with this technology. See, Hill (1996), supra.

The method and kit of the invention find numerous suitable applications, for example, in the food and cosmetic industry, as well as for the clinical diagnostic industry, e.g. for the detection of general or specific microorganisms and viruses, with simple instrumentation, and unskilled technicians.

EXAMPLES

Example 1

Typical PCR Reaction Components & Conditions

A master pre-mix for a standard 50 $\mu$l reaction (may be reduced to as small as a 10 $\mu$l reaction) is prepared as follows.

24 $\mu$l ultra purified water free of nucleases, proteases, heavy metals and DNA/RNA are mixed with 5 $\mu$l of a 2% solution of PVPP (polyvinylpolypyrrolidone) in ultra purified water, 5 $\mu$l of 10×PCR buffer (100 mM tris-HCl, pH 8.3, 500 mM KCl in ultrapure water), 5 $\mu$l of $MgCl_2$ (25 mM solution in ultrapure water), 1.25 $\mu$l of each primer (2 solutions at 50 ng/$\mu$l in ultrapure water), 1 $\mu$l of each dNTP (4 solutions at 10 mM in ultrapure water), 2.5 $\mu$l of enzyme (AmpliTaq LD at a 1:5 dilution in ultrapure water, Perkin-Elmer) and 2 $\mu$l of DNA template preparation as described below.

The mixture is then cycled under the following conditions: 30 sec at 95° C., 30 sec at 58° C. and 60 sec at 74° C. Each cycle is repeated 30–50 times depending on the sensitivity needed (determined by sample type and sample preparation, empirically).

Example 2

Sample Preparation

The conditions for the preparation of the sample are determined empirically based on the type and amount of the expected interfering substances to be present in the sample. However, once the proper blend of sample is finalized, a simple boil DNA extraction for 10 min is conducted prior to utilizing the sample as DNA template in the reaction.

To test for sterility of shelf stable commercially sterile pudding, for example, the pudding is diluted in ultrapure water 1:30 times, and boiled for 10 min before adding the pudding sample to a PCR pre-mix.

Example 3

Beacon Synthesis

Custom oligonucleotides having specified nucleotide sequences, a 5'-methoxytrityl protected $C_6$ thio group, and a 3'-$C_7$ amino linker group were utilized as starting materials for the synthesis. The synthetic sequence first converts the amine group of the oligomer to its dabcyl amide derivative, removes the methoxytrityl protective group, and converts the resulting thiol to edans or fluorescein thioether derivatives. Tyagi and Kramer's general synthetic strategy is employed by following Tyagi's supplemental procedures. See, Tyagi, S. And Kramer, R. R.,Molecular Beacons: Probes that Fluoresce upon Hybridization. Nature Biotechnology 14:303–308 (1996); modified as described here under the advise of Tyagi, S., Preparation of Molecular Beacons, Private Communication (1996).

Tyagi's procedure was modified for the present work in several ways, most significantly by changing reaction conditions during attachment of the edans of fluorescein groups, deletion of the precipitation step during the purification of the dabcylated intermediate and deletion of both HPLC and precipitation steps during purification of the final beacon product. In our hands, the precipitation of the dabcyl intermediate and the beacon product from ethanolic solution either did not occur or resulted in substantial losses of material. Under the conditions described here, conversion of the dabcyl intermediate to the beacon proceeded cleanly and, in many cases, HPLC purification of the product afforded little benefit.

DETAILED PREPARATION OF CODE 23 S-B'-FLUORESCEIN BEACON

Example 4

Reconstitution of DNA Oligomer

The DNA oligomer is a lyophilized solid obtained from Midland Certified Reagent Co. (Lot 021098-175, 2008 nmoles). It was dissolved in 3.0 m/L 0.1 M carbonate buffer (pH=8.5) and 500 $\mu$l used for the following dabcylation reaction.

Example 5

Conversion of Oligomer to Dabcyl Derivative

Aliquots (10 μL) of a saturated solution of se-dabcyl (Molecular Probes, 4-((4-dimethylamino)phenyl)azo) benzoic acid, succinimidyl ester) in dimethylformamide (DMF) were added at approximately 30 min intervals to the stirred oligomer. The se-dabcyl reagent was made by mixing 12.2 mg se-dabcyl with 110 μL DMF. A total of 10 aliquots are added. The reaction was allowed to proceed at ambient temperature for about 29 hours.

Example 6

Purification of the Dabcyl Intermediate

The reaction mixture was transferred to a small centrifuge tube, centrifuged for 4 min. at 14000 rpm, and the supernatant transferred to a second centrifuge vial. Residual material in the reaction flask was washed with a total of 400 μL of 0.01M triethylammonium acetate (TEAA, pH=6.5), and the washings used to resuspend the solids from the first centrifugation. After centrifugation, the supernatant was added to that from the first centrifugation. The total volume of the combined supernatants was reduced to 500 μL by vacuum evaporation (Speed Vac). Unreacted se-dabcyl and other relatively small compounds were separated from the dabcyl derivative and other oligomeric species by gel permeation chromotography using an NAP-5 (Pharmacia) column and 0.01 M TEAA mobile phase. See below, for specific procedure used for a NAP-5 column). The fraction containing the higher molecular weight materials was concentrated to slightly less than 500 μL. Dabcyl intermediate was then separated from other oligomers via reversed phase HPLC (Vydac C 18 column, see note 2 for procedure) of two approximately 250 μL injections.

Under the HPLC conditions employed, the present dabcyl intermediate had a retention time of about 28–30 min and yields yellowish fractions. Several 1 mL fractions in this region were pooled and concentrated to 500 μl. The dabcyl intermediate was desalted by NAP-5 column chromatography using 0.01M TEAA mobile phase arid the resulting 1 mL eluate concentrated to about 250 μL.

Example 7

Conversion of Dabcyl Intermediate to Fluorescein Beacon

After removing a 5 μL sample (for analysis by HPLC, note 3), 10 μl of a freshly prepared aqueous silver nitrate (0.27 g $AgNO_3$/10 mL, about a 5-fold molar excess of $AgNO_3$ over DNA oligomer, solution was added and the mixture allowed to react for 30 min at room temperature with intermittent mixing. See, Connolly, B. A., Chemical Synthesis of Oligonucleotides Containing a Free Sulfhydryl Group and Subsequent Attachment of Thiol Specific Probes, Nucleic Acids Research 13 (12): 4485–4503 (1985).

15 μL of freshly prepared aqueous dithiothreitol solution (0.23 dithiothreitol/10 mL, about a 7-fold molar excess over DNA oligomer) were added and reaction proceeded for 5 min at ambient temperatures with occasional stirring. The reaction mixture was centrifuged, and the supernatant transferred to a fresh reaction vial. Another 5 μL analytical sample was removed. The pH of the remaining supernatant was then adjusted to about 9.0 by treating with an equal volume (about 265 μL) of 0.2M carbonate (pH=9.0). To this, 25 μL of a freshly prepared solution of 5-IAF in dimethylsulfoxide (DMSO) was added. This solution contained about 10.9 mg 5-IAF (Molecular Probes, 5-IAF iodoacetamidofluorescein) in 125 μL DMSO. This is about a 13.5-fold excess of 5-IAF over oligomer and about a 2.5-fold molar excess of 5-IAF. over total sulfhydryl groups (deprotected DNA oligomer and dithiothreitol). After brief mixing, reaction was allowed to proceed for about 3.5 days at refrigerator temperatures (about 5° C.).

Example 8

Purification of Fluorescein Beacon

The volume of the reaction mixture was reduced to 500 μL and the crude reaction mixture chromatographed on an NAP-5 column using 2 mM Tris buffer (pH=8.3, Trizma, Sigma). The higher molecular weight fraction was concentrated to 500 μL and again purified on an NAP-5 column with Tris mobile phase. The volume of the final preparation was adjusted to 500 μl.

Example 9

Fluorescein Beacon Yield

The concentration on the final beacon product was determined spectrophotometrically (absorbance at 260 nm) after correcting the observed reading for the spectral contribution of the dabcyl and fluorescein groups.

Abs 260 (corr)=Abs 260 (obs)/1.14

The yield from this preparation was about 31% based on amount of starting DNA oligomer.

Example 10

NAP-5 Gel Permeation Chromatography

A NAP-5 column was equilibrated to the particular mobile phase and used according to the manufacturer's directions. This entails allowing the excess liquid present with the commercial column to elute, equilibration with about 10 mL of mobile phase, and loading the sample (volume 500 μl max). During loading, all of the liquid phase was allowed to enter the column bed and eluting material is discarded. Subsequently, a small centrifuge vial was positioned to collect eluant and 1.0 mL of mobile phase was added. The approximately 1.0 mL eluting contains most of the desired DNA oligomeric materials.

Example 11

Reversed Phase HPLC

A Waters instrument equipped with dual pumps, a solvent programmer (Waters 600E System Controller), Vydac C18 RP column, UV-Vis detector (Waters 486 Tunable Absorbance Detector), A/D converter (PE Nelson 900 Series Interface), computer with associated chromatographic software (PE Nelson Turbochrom), and manual injector was used. The column flow rate used was 1.0 mL/min, and the detection wavelength was usually 260 (sometimes 490) mm. A linear solvent gradient changed solvent composition from 100% A to 100% B over a 40 min period. Solvent A was an 80:20 (v/v) mixture of 0. IM TEAA (pH=6.5) and acetonitrile; solvent B a 30:70 mixture of 0.1M TEAA and acetonitrile.

Example 12

Analytical HPLC

The composition of the starting material, the final product and intermediate preparations (both the protected and deprotected dabcyl species) were monitored by HPLC under conditions identical to those described below but using 20 μL injections. The aliquots noted above were concentrated enough that, after dilution about 10-fold (usually in 0.1M TEAA or 2 mM Tris buffers), adequate responses were detected.

Edans

The edans beacon referred to above results from reacting the deprotected sulfhydryl group with 1,5-IAEDANS (Molecular Probes, 1,5-IAEDANS stands for 5-((((2-iodoacetyl)amino)ethyl)amino)naphthalene-1 sulfonic acid).

References

1. Tyagi, S. And Kramer, R. R., 1996. Molecular Beacons: Probes that Fluoresce upon Hybridization. Nature Biotechnology 14:303–308.
2. Tyagi, S., 1996. Preparation of Molecular Beacons. Private communication.
3. Connolly, B. A. 1985. Chemical Synthesis of Oligonucleotides Containing a Free Sulfhydryl Group and Subsequent Attachment of Thiol Specific Probes. Nucleic Acids Research 13(12): 4485–4503.

What is claimed as novel & unobvious in U.S. Letters Patent is:

1. An in vitro method of detecting the presence of a microbe in a food sample, comprising:

(a) forming a polymerase chain reaction mixture by combining (1) a predetermined volume of a food sample to be tested for the presence of a universal bacteria nucleic acid sequence comprising 5'-CCACCGAATCTTCGTCGGTGG-3' (SEQ. ID. NO.: 144) and sequences upstream and downstream of the universal bacteria nucleic acid sequence (2) known amounts of a first nucleic acid primer and a second nucleic acid primer for binding to the upstream sequence and the downstream sequence, respectively, wherein a fluorogen is connected to one end of the first or second primer, and a (3) polynucleotide containing a single-stranded DNA probe that specifically hybridizes to SEQ. ID. NO.: 144 and wherein the polynucleotide assumes a stem-loop structure in the absence of the universal or bacterial nucleic acid sequence wherein the polynucleotide comprises a DNA internal segment being complementary to at least a portion of the universal bacterial nucleic acid sequence and a first and a second DNA arm segment adjoining the DNA internal segment, each of the arm segments comprising nucleotide sequences such that the arm segments are complementary to one another and (4) polymerase chain reaction reagents;

(b) forming a polymerase chain reaction product by cycling the polymerase chain reaction mixture under conditions whereby the universal bacterial nucleic acid sequence is replicated to from about 0.25 to about 10,000 $\mu$g nucleotide product/$\mu$l mixture;

(c) quenching any primer not bound to the upstream or the downstream sequences in the polymerase chain reaction product;

(d) hybridizing the DNA probe to the universal bacterial nucleic acid sequence, if present, and change the conformation of the stem-loop structure, the presence of a microbe in the sample is determined by detecting the conformational change in the stem-loop structure of the polynucleotide; and (e) determining whether or not the universal bacterial nucleic acid sequence is present in the polymerase chain reaction product, the presence of the universal bacterial nucleic acid sequence detecting the presence of a microbe in the food sample.

2. The method in accordance with claim 1, wherein the internal DNA segment and the arm segments comprise a sequence complementary to at least a portion of a contiguous universal bacterial nucleic acid sequence.

3. An in vitro method of detecting the presence of a microbe in a food sample, comprising the steps of:

(a) forming a polymerase chain reaction mixture by combining (1) a predetermined volume of a food sample to be tested for the presence of a nucleic acid sequence comprising a universal bacteria nucleic acid sequence comprising 5'-CCACCGAATCTTCGTCGGTGG-3' (SEQ. ID. NO.: 144) of a microbe and sequences upstream and downstream of the universal bacterial nucleic acid sequence (2) known amounts of a first nucleic acid primer and a second nucleic acid primer for binding to the upstream sequence and the downstream sequence, respectively, wherein a fluorogen is connected to one end of the first or second primer and (3) polymerase chain reaction reagents;

(b) forming a polymerase chain reaction product by cycling the polymerase chain reaction mixture under conditions whereby the universal bacterial nucleic acid sequence is replicated to from about 0.25 to about 10,000 $\mu$g nucleotide product/$\mu$l mixture;

(c) adding to the polymerase chain reaction product a polynucleotide containing a single-stranded DNA probe that specifically hybridizes to SEQ ID NO: 144 and wherein the polynucleotide assumes a stem-loop structure in the absence of the universal bacterial nucleic acid sequence wherein the polynucleotide comprises a DNA internal segment being complementary to at least a portion of the universal bacterial nucleic acid sequence and a first and a second DNA arm segment adjoining the DNA internal segment, each of the arm segments comprising nucleotide sequences such that the arm segments are complementary to one another;

(d) quenching any primer not bound to the upstream or the downstream sequences in the polymerase chain reaction product;

(e) determining whether or not the universal bacterial nucleic acid sequence is present in the polymerase chain reaction product, the presence of the universal bacterial nucleic acid sequence detecting the presence of a microbe in the food sample; and (f) hybridizing the DNA probe to the universal bacterial nucleic acid sequence, if present, and change the conformation of the stem-loop structure, the presence of a microbe in the sample is determined by detecting the conformational change in the stem-loop structure of the polynucleotide.

4. The method in accordance to claim 3, wherein the internal DNA segment and the arm segments comprise a sequence complementary to at least a portion of a contiguous universal nucleic acid sequence.

5. An in vitro method of detecting the presence of a bacterium in a food sample, comprising the steps of:

forming a polymerase chain reaction mixture by combining (1) a predetermined volume of a food sample to be tested for the presence of a nucleic acid sequence comprising a universal nucleic acid sequence comprising 5'-CCACCGAATCTTCGTCGGTGG-3' (SEQ. ID. NO: 144) and sequences upstream and downstream of the universal or specific nucleic acid sequence, (2) known amounts of a first nucleic acid primer and a second nucleic acid primer for binding to the upstream sequence and the downstream sequence, respectively, wherein a fluorogen is connected to one end of the first or second primer, and (3) polymerase chain reaction reagents;

forming a polymerase chain reaction product by cycling the polymerase chain reaction mixture under conditions whereby the universal or specific nucleic acid sequence is replicated to from about 0.25 to about 10,000 $\mu$g nucleotide product/$\mu$l mixture;

adding to the polymerase chain reaction mixture or to the polymerase chain reaction product a polynucleotide comprising a DNA internal segment specifically hybridizes to SEQ ID NO: 144 and a first and a second DNA arm segment adjoining the DNA internal segment, each of the arm segments comprises nucleotide sequences such that the arm segments are complementary to one another, the polynucleotide assuming a stem-loop structure in the absence of the universal or specific nucleic acid sequence;

hybridizing the DNA probe to at the universal nucleic acid sequence, if present, and changing the conformation of the stem-loop structure;

quenching any primer not bound to the upstream or the downstream sequences in the polymerase chain reaction product; and detecting the presence of a bacterium in the food sample by determining whether or not the universal or specific nucleic acid sequence is present in the polymerase chain reaction product by detecting whether there was a conformational change in the stem-loop structure of the polynucleotide.

6. The method in accordance with claim 5, wherein a change in conformation of the stem-loop structure is detected by a fluorescent detection system.

7. The method in accordance with claim 6, wherein a change in conformation of the stem-loop structure results in fluorescence from the polynucleotide.

8. The method in accordance with claim 5, wherein the polynucleotide is added to the polymerization reaction mixture.

9. The method in accordance with claim 5, wherein the polynucleotide is added to the polymerization reaction product.

10. The method in accordance with claim 5, wherein any primer not bound to the upstream or the downstream sequences in the polymerase chain reaction product is quenched by adding to the polymerase chain reaction product an oligonucleotide that is complimentary to the primer and has a quencher attached to said oligonucleotide.

11. The method in accordance with claim 5, wherein the fluorogen is connected to the 5' end of the first primer or the second primer and any primer that is not bound to the upstream or the down stream sequences in the polymerase chain reaction product is quenched by adding to the polymerase chain reaction product an oligonucleotide that is complimentary to the primer and has a quencher attached to the 3' end of said oligonucleotide.

12. The method in accordance with claim 5, wherein the fluorogen is fluorescein and the quencher is dabcyl.

13. The method in accordance with claim 5, wherein the cycling is conducted about 1 to 30 times at alternative temperatures of about 95° C. to about 58° C., about 58° C. to a 74° C. or 74° C. to 95° C.

14. The method in accordance to claim 5, wherein the internal DNA segment and the arm segments comprise a sequence complementary to at least a portion of a contiguous universal nucleic acid sequence.

15. The method in accordance with claim 5, wherein the ratio of polynucleotide and primer concentrations is about 0.6 to 1 to about 1.6 to 1.

16. The method in accordance with claim 5, further comprising adding to the polymerase chain reaction product single-stranded DNA that is complementary to at least a portion of the universal nucleic acid sequence and hybridizing the DNA to at least a portion of the universal nucleic acid sequence, if present, to form double stranded nucleic acid; and detecting the presence of the universal nucleic acid sequence in the polymerase chain reaction product by detecting any double stranded DNA.

17. The method in accordance with claim 16, wherein the formation of double stranded nucleic acid is detected by a fluorescent detection system and wherein when no universal nucleic acid is present and replicated by the polymerase chain reaction in the sample the internal DNA segment remains single stranded and flourescence is detected, and when there is nucleic acid present and replicated by the polymerase chain reaction, its bacterial nucleic acid sequence is double stranded and operatively bound to the fluoregenic agent fluoresces.

18. The method of claim 17, wherein the internal DNA segment and the universal nucleic acid sequence, if present in the polymerase reaction product, are separated prior to the fluorescence detection.

19. The method of claim 18, wherein the internal DNA segment and the universal nucleic acid sequence, if present in the polymerase reaction product, are separated by electrophoresis.

20. The method of claim 19, further comprising staining the internal DNA segment and the universal nucleic acid sequence, if present in the polymerase reaction product, with a DNA stain that operatively binds to double stranded nucleic acid, but not to single stranded nucleic acid.

21. The method in accordance with claim 20, wherein the DNA stain is ethidium bromide and fluorescence is detected under ultraviolet light.

* * * * *